(12) United States Patent
DiChiara

(10) Patent No.: US 8,641,188 B2
(45) Date of Patent: Feb. 4, 2014

(54) EYEWEAR FRAMES WITH MAGNETIC LENS ATTACHMENTS

(75) Inventor: Carmine S. DiChiara, Warren, NJ (US)

(73) Assignee: Switch Vision, LLC, Fairfield, NJ (US)

( * ) Notice: Subject to any disclaimer, the term of this patent is extended or adjusted under 35 U.S.C. 154(b) by 100 days.

(21) Appl. No.: 13/250,053

(22) Filed: Sep. 30, 2011

(65) Prior Publication Data

US 2012/0019770 A1  Jan. 26, 2012

Related U.S. Application Data

(63) Continuation-in-part of application No. 12/772,110, filed on Apr. 30, 2010, now Pat. No. 8,092,007, which is a continuation-in-part of application No. 11/658,390, filed as application No. PCT/US2007/000681 on Jan. 11, 2007, now Pat. No. 7,850,301.

(60) Provisional application No. 60/758,562, filed on Jan. 13, 2006.

(51) Int. Cl.
*G02C 1/04* (2006.01)

(52) U.S. Cl.
USPC .............................. 351/86; 351/106; 351/154

(58) Field of Classification Search
USPC ......... 351/83, 84, 85, 86, 103, 106, 107, 108, 351/109, 154, 41
See application file for complete search history.

(56) References Cited

U.S. PATENT DOCUMENTS

| | | | | |
|---|---|---|---|---|
| 5,321,442 | A * | 6/1994 | Albanese | 351/44 |
| 6,478,420 | B2 * | 11/2002 | Xiang | 351/47 |
| 6,592,220 | B1 * | 7/2003 | Cheong | 351/106 |
| 7,600,870 | B2 * | 10/2009 | Zelazowski | 351/47 |
| 7,850,301 | B2 * | 12/2010 | DiChiara | 351/106 |
| 8,092,007 | B2 * | 1/2012 | DiChiara | 351/106 |
| 2005/0007546 | A1 * | 1/2005 | Pilat et al. | 351/154 |
| 2007/0013863 | A1 * | 1/2007 | Zelazowski | 351/47 |

FOREIGN PATENT DOCUMENTS

| | | |
|---|---|---|
| TW | M273729 | 8/2004 |
| TW | M241681 | 8/2005 |

* cited by examiner

*Primary Examiner* — Hung Dang
(74) *Attorney, Agent, or Firm* — Cowan, Liebowitz & Latman, P.C.; Mark Montague

(57) ABSTRACT

The present invention illustrates various methods of attaching a pair of eyeglass lenses or a lens shield to an eyeglass frame using magnets or magnetically attractive material. The magnetic attachment methods are beneficial because they allow the user to have interchangeable lenses or shields for indoor and outdoor use, enhancing their visual acuity during work or play. The lenses may be tinted, prescription, protective eyewear, or plano. The magnetic lenses are convenient and user friendly, allowing intuitive, tool-less interchangeability with no need to twist or stress the frame. These methods of attachment require no specific instructions or tools when the user replaces lenses.

10 Claims, 29 Drawing Sheets

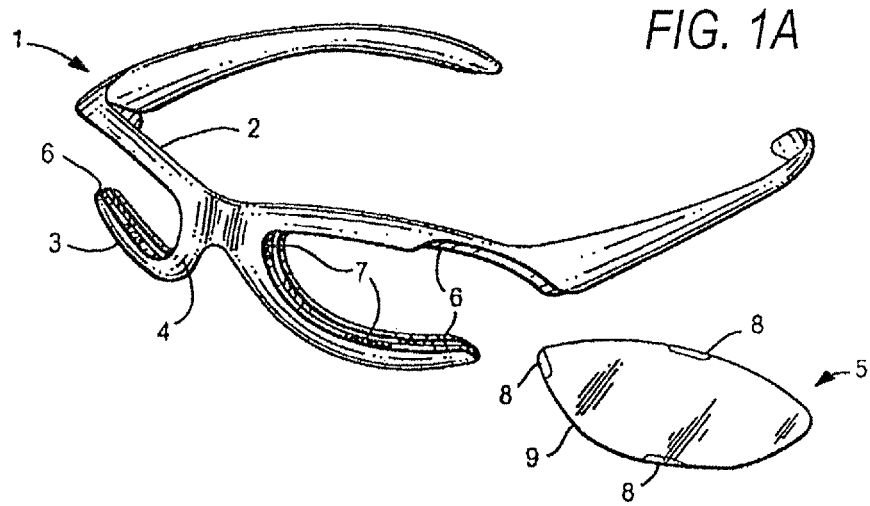
FIG. 1A
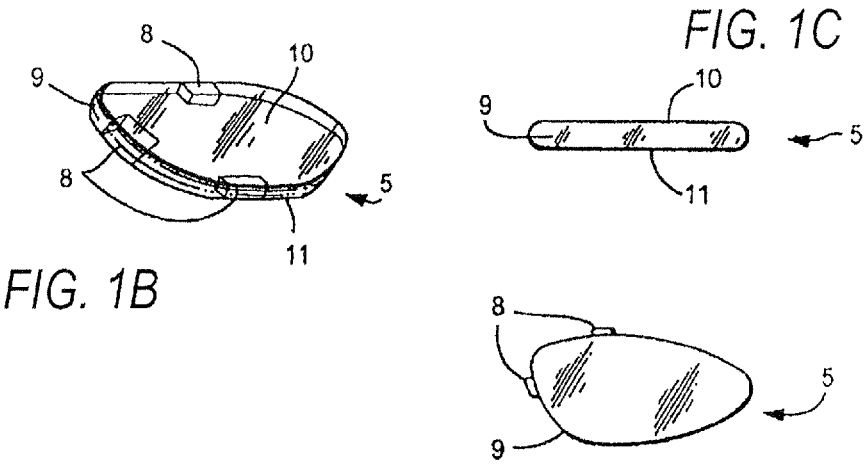
FIG. 1C
FIG. 1B
FIG. 1D

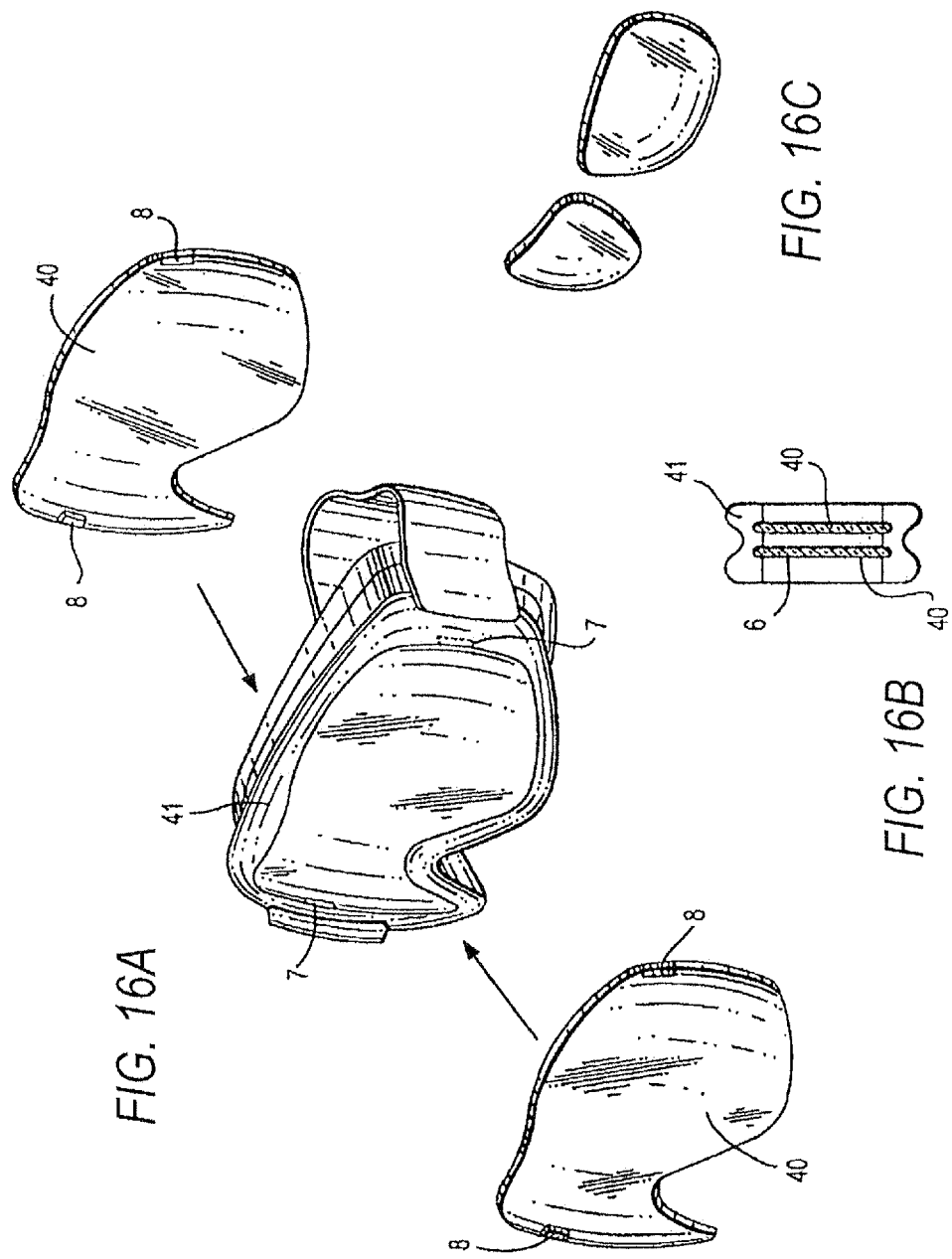

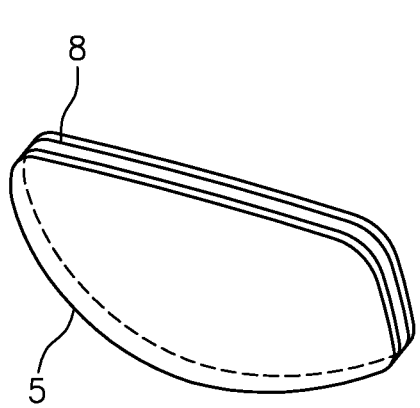
FIG. 29A          FIG. 29B
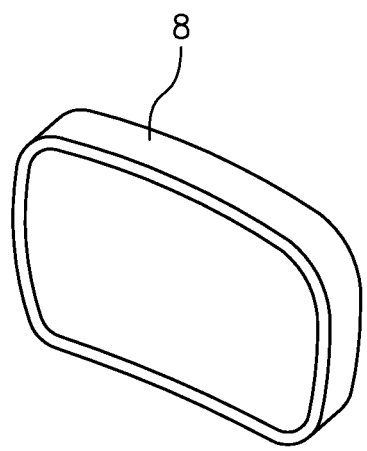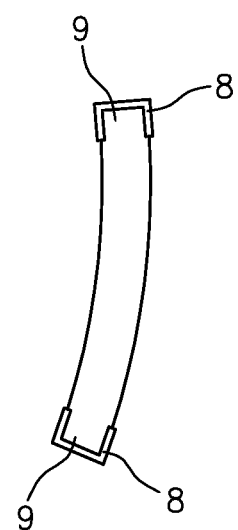
FIG. 30A          FIG. 30B

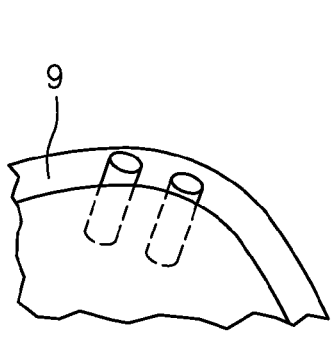
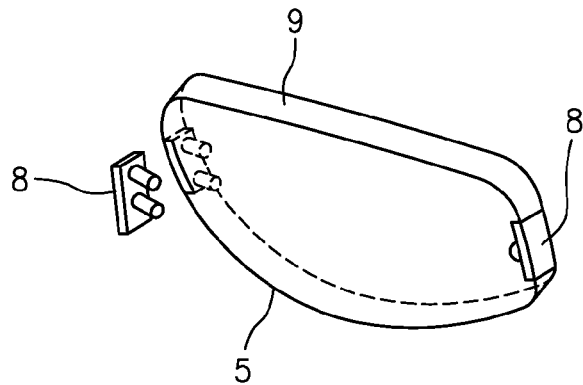
*FIG. 32A*    *FIG. 32F*
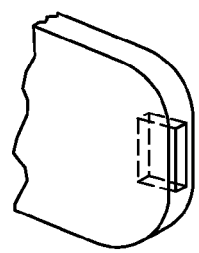
*FIG. 32B*
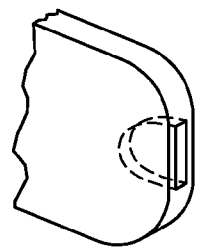
*FIG. 32C*
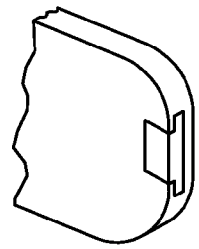
*FIG. 32D*
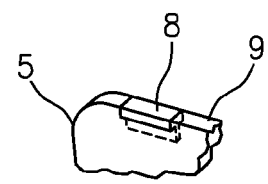
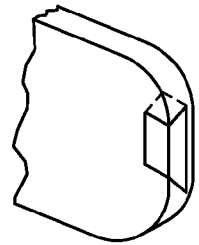
*FIG. 32E*
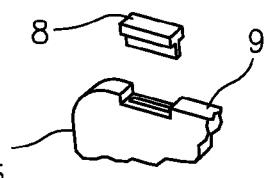
*FIG. 32G*

EYEWEAR FRAMES WITH MAGNETIC LENS ATTACHMENTS

REFERENCE TO RELATED APPLICATIONS

This application is a continuation-in-part of application Ser. No. 12/772,110 filed Apr. 30, 2010, now U.S. Pat. No. 8,092,007, which is a continuation-in-part of application Ser. No. 11/658,390 filed Jan. 25, 2007, now U.S. Pat. No. 7,850,301, which is the U.S. National Phase of PCT/US2007/00681, filed Jan. 11, 2007, claiming priority to U.S. Provisional Application Ser. No. 60/758,562, which was filed on Jan. 13, 2006.

FIELD OF THE INVENTION

The present invention relates to eyewear frames with magnetic lens attachments. More particularly, the present invention relates to eyeglass frames with interchangeable prescription or plano lenses and/or plano shields that can be interchanged by the user in a simple, and convenient manner and that are easily releasably attached to the frame.

BACKGROUND OF THE INVENTION

A typical pair of eyeglasses includes a pair of lenses or a single shield mounted to a frame that may include rims around the lenses; a brow bar; a bridge piece connecting the inner ends of the rims; and two temple pieces attached to the outer ends of the rims for resting the glasses on the user. Lenses are typically mounted to the eyeglass frame by a screw or other fastening device that tightens the rim around the lens. In the conventional configuration, the screw must be removed before the lens may be removed. The screw is often small and identifying the size and type of screw can require the user to strain his or her eyes. Removing the screw requires that the user have a screw driver or other tool that fits the particular screw in that pair of eyewear. Users will often not have the proper screwdriver. If the screw is broken or stripped, the user must then find a suitable replacement screw. This is inconvenient for the user as different eyeglasses use different kinds of screws which may have different head types and sizes. These different screws will often not work in different pairs of eyeglasses or with different screwdrivers. Additionally, if the screw breaks while in the glasses, the user may have difficulty removing the broken screw. Users may also desire to change lenses while wearing the glasses to accommodate different lighting conditions. Mounting lenses to the frame using screws can make this process highly inconvenient for the user.

Recently, prescription lenses have been developed with notches to make them interchangeable in brow bar designs if desired. This requires a forcing of the brow bar to go over the notches in the lenses. This technique can be quite cumbersome to work with in both the insertion and removal of the lenses.

Examples of various prior eyewear are disclosed in the following patents and publications, the disclosures of which are hereby incorporated herein by reference: U.S. Pat. No. 3,565,517 to Gitlin et al, U.S. Pat. No. 3,838,914 to Fernandez, U.S. Pat. No. 5,321,442 to Albanese, U.S. Pat. No. 6,592,220 to Cheong, and U.S. Pat. No. 6,866,386 to Chen; Japanese patent applications 59072417, 60140316, and 2004021086; and PCT patent application WO 96/37800.

Accordingly, there is a need for providing an easily replaceable, convenient mechanism for coupling interchangeable eyeglass lenses to frames.

SUMMARY OF THE INVENTION

An object of the present invention is to provide a magnetic coupling system for eyeglass lenses. More specifically, it is an object of the present invention to provide an interchangeable magnetic lens system.

A further object of the present invention is to provide magnetic material attached to an eyeglass frame for releasably coupling lenses to the frame.

Another object of the invention is to provide magnets attached to the lenses for attracting to the magnetic forces of the magnetic material in the eyeglass frame.

Yet another object of the invention is to provide user-friendly and interchangeable magnetic lenses for eyeglasses.

Still another object of the invention is to provide various coupling methods for securing the magnetic lenses to the frames that have the magnetic material.

Another object of the invention is to allow the user to change their lenses easily, as opposed to relying on an optician or eyecare professional to change the lenses.

Yet another object of the invention is to provide interchangeable magnetic lenses or shields with different treatment tints or coatings.

These objects are basically attained by providing a single shield-type lens or a pair of interchangeable lenses that may be placed in position in eyeglass frames using magnetic members to lock the respective lenses in place. The lenses may be embedded with or otherwise support magnets or a magnetic material. The magnets or magnetic material in the lenses are attracted to corresponding magnets or magnetic material in a pair of eyeglass frames.

It is to be understood that in all embodiments of the present invention, the lenses and frames may both be mounted with permanent magnets. Alternatively, either the lenses or the frame may have permanent magnets secured to one or the other, while the other of the lenses and the frame may have secured to it, or may be made of, magnetically attractive material, such as ferrous metal.

The magnets or magnetic material can be positioned at various points of the frame and lens, such as in the annular areas or inner circumference of the frame and in the brow bar or nosepiece. The lenses are easily removable, providing a rapid and simple interchange of lenses. The magnets or magnetic material in the lenses can be mounted in a number of ways, including a 3-piece mounted frame, generally suitable for rimless frames. Another option is to provide a lens that fits into frames having a closed annular shelf with magnets on opposite sides, where the shelf prevents the lens from falling backwards out of the frame.

Other objects, advantages, and salient features of the present invention will become apparent from the following detailed description, which, taken in conjunction with the annexed drawings, discloses preferred embodiments of the invention.

BRIEF DESCRIPTION OF THE DRAWINGS

FIG. 1A is a front view of a pair of eyewear frames and detached lens, both comprising magnets according to a first embodiment of the invention;

FIG. 1B is a front view of a lens with magnets or magnetic material embedded therein;

FIG. 1C is a side view of a lens having no magnets or magnetic material;

FIG. 1D is a front view of a lens with magnets or magnetic material secured to the lens so that said magnets or magnetic material protrude beyond the edge of the lens;

FIG. 16A is a perspective view of an embodiment of the present invention having a goggle-style frame and two shield-style lenses;

FIG. 16B is a cross-sectional view of an embodiment of the present invention having a goggle-style frame and two shield-style lenses;

FIG. 16C is a front view of a pair of lenses that could be combined with the embodiment shown in FIG. 16A;

FIGS. 29A-B is a perspective view of a lens with a cavity of a certain shape running along the peripheral edge of the lens and a magnet having a corresponding shape.

FIGS. 30A-B is a perspective view of a lens with a cavity of a certain shape running along the peripheral edge of the lens and a magnet having a corresponding shape.

FIGS. 32A-G is a side view of lenses with cavities of a certain shape on the side edge of the lens and magnets of corresponding shapes.

DETAILED DESCRIPTION OF THE INVENTION

Figure 1E:
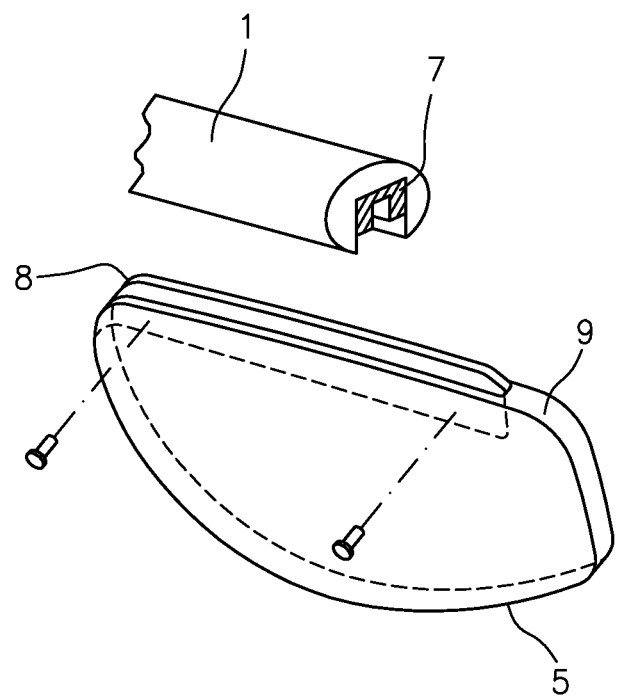
FIG. 1E is a front view of a lens with a single magnet or magnetic material extending from a substantial portion of an upper edge of the lens.

As used herein, the term "lens" will be understood to include eyeglass lenses of a variety of shapes and sizes as well as one or more shield style lenses. As used herein, the term "frame" will be understood to include blade-style frames, goggle-style frames, conventional frames, and any other style of eyewear frame. As used herein, the term "plano lens" shall refer to lenses and shields that are not made to fill a wearer's prescription. The term "prescription lens" shall refer to lenses and shields that are made to fill a wearer's prescription as used in this description. "Plano lens" and "prescription lens" are used interchangeably throughout this specification. The terms "magnets," "magnetic member," "magnetized material," and "magnetic material," as used in this description, refer to magnets or material that has magnetic properties or is capable of attracting a magnet. As such, "magnets," "magnetic member," "magnetized material," and "magnetic material," are interchangeable in this description. A "magnetic member" as used herein is a component of an eyeglass assembly that is either a magnet or is made from magnetically attractive material. An "eyeglass assembly," as used in this description, refers to an assembled pair of eyeglasses including a frame and at least one lens.

FIG. 1A shows an embodiment of the present invention. A pair of eyeglass frames 1 includes at least one magnet or element of magnetically attractive material 7 embedded in the frame 1. In FIG. 1A, each side of the frame 1 includes a portion of a rim 2 and 3 for supporting a lens 5. Each rim portion 2 and 3 includes a recess 6 into which a lens 5 may be received. The recess 6 may extend toward the nosepiece 4. Magnets or magnetically attractive material 7 are embedded into the recesses 6 in the rim portions 2 and 3 of the frame 1. Preferably, at least one magnet or element of magnetically attractive material 7 is located on each side in the recess 6 of the frame 1 that may receive a lens 5. Magnets or magnetic material having opposing and attractive forces 8 are attached to the corresponding ends of the eyeglass lenses 5 such that, when the lenses 5 are held close to the frames 1, the attractive forces of the positively and negatively charged magnets pull the magnets 8 of the lenses 5 towards the magnets 7 of the frames 1. The magnets 7 are preferably embedded in the recess 6 of the frames 1 and the corresponding edge(s) 9 of each of the lenses 5. This formation of the magnets provides a fully seated lens that is held in place through magnetic forces, as seen in FIG. 2.

FIG. 1B shows a lens with magnets or magnetic material 8 embedded therein. A lens 5 has a front surface 10, a rear surface 11 and an edge 9. FIG. 1C shows a lens 5 laying on its rear surface 11, with its edge 9 facing the reader, and its front surface 10 pointing toward the top of the page. The lens 5 in FIG. 1C is similar to the lens in FIG. 1B with no magnets or magnetic material embedded in the lens 5. In the lens shown in FIG. 1B, the magnets or magnetic material 8 secured to the lens 5 lies flush with the edge 9 of the lens 5. The magnets or magnetic material 8 may be flush with the front 10 or rear 11 surfaces of the lens 5. It is not necessary that the magnet or magnetic material 8 lie flush with or break the plane of the edge 9 or the front 10 or rear 11 surfaces. The lens may cover the magnet or magnetic material as long as the magnet or magnetic material, when assembled, is sufficiently close to the corresponding magnets or magnetic material in the frame that the magnets or magnetic material in the frame and the lens attract one another.

FIG. 1D shows another lens according to the present invention. Magnets or magnetic material 8 protrude beyond the edge 9 of the lens 5.

Figure 2:
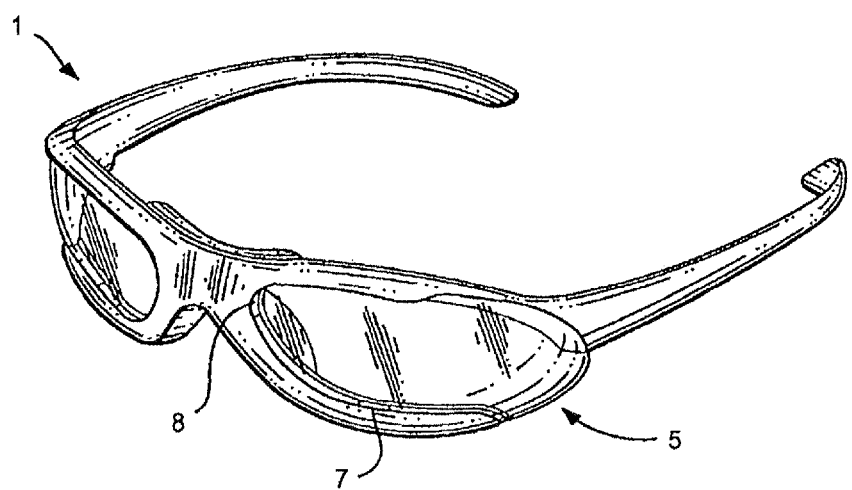
FIG. 2 is a front view of a pair of eyewear frames, as seen in FIG. 1, with the lenses mounted to the frame.

FIG. 1E shows a protruding magnet or magnetic material 8 extending from an edge 9 of a lens 5 in accordance with an embodiment of this invention. The magnet or magnetic material may extend from the edge 9 for a portion of the circumference of the edge. In some embodiments, the magnet or magnetic material 8 may extend from all, or substantially all, of the circumference of the edge 9 of the lens 5. The magnetic material 8 may be attached to the lens by any known method, such as a press fit into a pocket in the edge 9 of the lens 5, with or without adhesive or mechanical fasteners, such as, but not limited to, screws, bolt and nut, roll pins, and press fit pins.

The protrusion or tab of magnetic material may be accepted in a suitably configured magnet or magnetic material 7 in the frame 1.

Figure 1F:
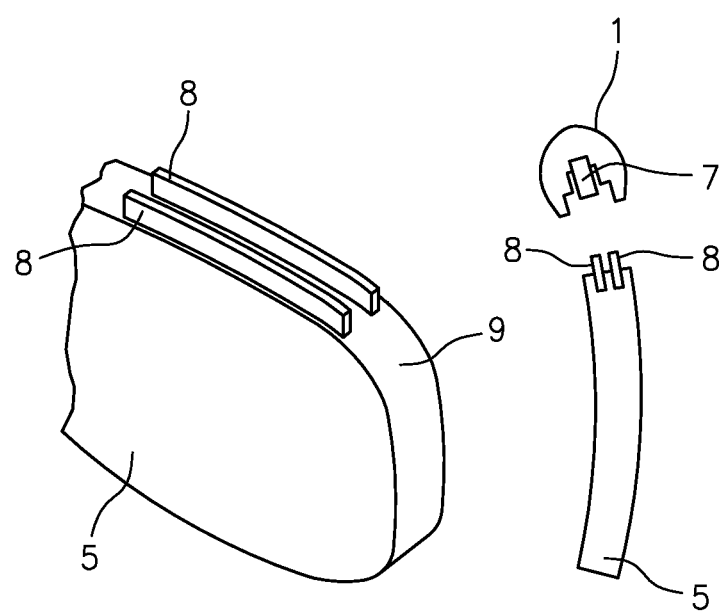
FIG. 1F is a front view of a lens with a plurality of magnets or magnetic materials extending from a substantial portion of an upper edge of the lens.

FIG. 1F, similar to FIG. 1D or 1E, shows two protrusions or tabs of magnets or magnetic materials 8 extending from the edge 9 of a lens 5. As shown, the magnetic materials 8 are generally parallel and coextensive. In other embodiments, the magnetic materials 8 may differ from each other in length, thickness, height and cross section, and may or may not be parallel.

The protrusions or tabs of magnetic materials may be accepted in a suitably configured magnet or magnetic material in the frame. In the embodiment shown in FIG. 1E, a magnet or magnetic material 7 in the frame 1 is configured to fit within oppositely inward facing surfaces of the protrusions or tabs. Alternately, or additionally, a magnetic material or materials 7 may be placed in the frame 1, configured to align with the oppositely outwardly facing surfaces of the magnetic materials 8 of the lens 5.

FIG. 2 shows a front view of an assembled eyeglass frame assembly according to an embodiment of the present invention. The frame 1 contains magnets or magnetic material 7 embedded therein. The lens 5 also contains magnets or magnetic material 8 embedded therein. The attractive forces between the magnets or magnetic material in the frame 7 and the magnets or magnetic material in the lenses 8 secure the lenses 5 to the frame 1.

Figure 3A:
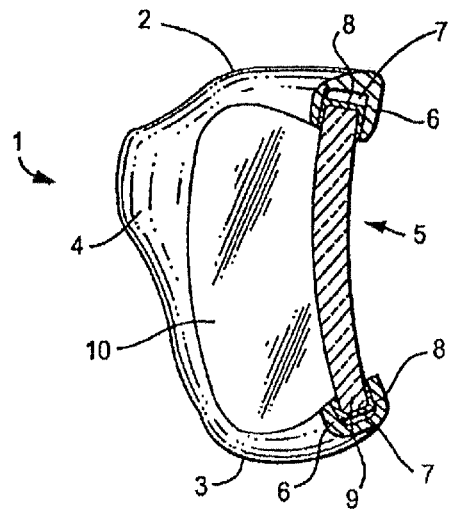
FIGS. 3A and 3B are cross-sectional views of the eyewear frames, as seen in FIGS. 1 and 2, at the point of magnetic attachment.

The cross-sectional view of FIG. 3A depicts the point of contact between the lens 5 and the frames 1. The frames 1 include a first 2 and a second 3 rim section. The first 2 and second 3 rim sections have a recess 6 for receiving the lens 5. The recesses 6 are shaped to fit the contour of the lens edges. Typically the recesses 6 are U-shaped, for receiving an end of a lens 5. The nose piece 4 may also have a recess and contain magnetic material. Magnets or magnetic material 8 are secured to the outside of the lens 5, and are positioned near the magnets 7 in the frame 1. The figure shows the front surface of the eyeglasses with the front surface of the lens 10 facing toward the reader. The location of the edge 9 of the lens 5 can also be seen in the cross-section.

Figure 3B:
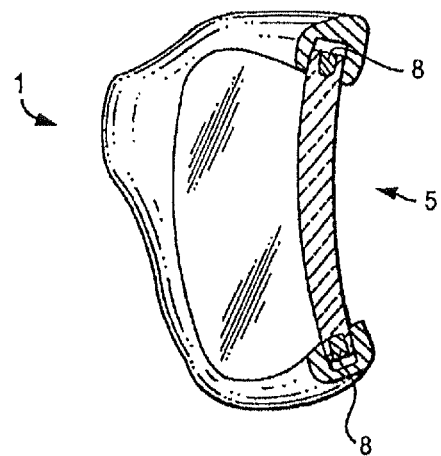

FIG. 3B illustrates a cross-section of the eyewear illustrated in FIG. 3A, but with a first and a second magnet 8 embedded in the lens 5. The magnetic lens 5 is snugly fitted to the frame 1 so as to not accidentally eject during normal use of the frame 1.

In another embodiment of the present invention, the magnets or magnetically attractive material may be embedded in the lenses so as to be flush with the surface of the lenses. The lenses would be received into a recess similar to that shown in FIGS. 1A, 2, 3A, and 3B, but without a lower rim section.

Figure 4:
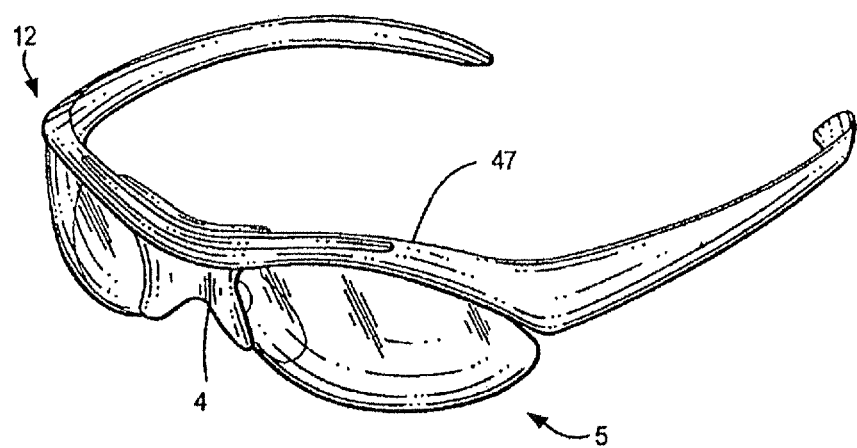
FIG. 4 is a front view of a 'blade'-style frame with magnetic lenses.

FIG. 4 shows another embodiment of the present invention. It is possible to attach lenses 5 containing magnets or magnetic material to 'blade'-style frames 12. A 'blade'-style frame 12 is a winged frame conventionally designed so that there are no rims surrounding the lower arcuate surfaces of the lenses 5. In other words, a 'blade'-style frame looks like a pair of lenses bordered by wings. Only the upper and nasal sections of the lenses 5 are engaged by the frame 12. The points of contact between the frame 12 and the lenses 5 comprise a first section of a recess located in the horizontal bridge portion 47 of the frame 12 and a second section of a recess located in the side wall adjacent to a nosepiece 4.

Figure 5A:
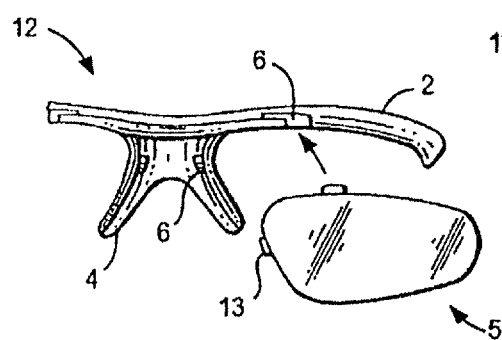
FIGS. 5A-5C are front views of an alternative embodiment having magnets protruding from the top and nasal area of the lenses, which are received into pockets containing magnetic material on the horizontal arm and nose piece of the frame.

FIG. 5A shows an embodiment of the present invention. The 'blade'-style frame 12, as seen in FIG. 4, can receive lenses 5 in a recess 6 of the upper rim portion 2 of the frame 12 and in a recess 6 in the side wall adjacent the nosepiece 4. The lens 5 includes tabs 13 protruding from the edge of the lens 5. Magnets or magnetic material may comprise or be attached to the tabs 13.

Figure 5B:
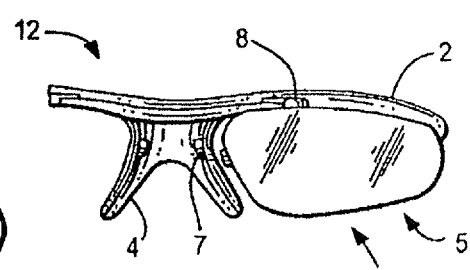

FIG. 5B shows the same embodiment of the present invention as FIG. 5A, with the lens in place in the frame. The frame 12 has magnets 7 positioned in the recess of the upper rim portion 2 of the frame 12 and the nosepiece 4. A lens 5 is positioned in the frame 12, preparing for the magnetic forces of the magnets or magnetic material embedded in the frame 7 and the magnets or magnetic material 8 embedded in the lens 5 to attract. The lens 5 has been inserted upwards into the recess in the upper rim portion 2 of the frame 12 where the tabs are received. Once the tab 13 is pulled into place by the nasal magnets 7, a second magnet embedded in a recess 6 in the upper rim portion 2 of the frame 12, pulls the tab 13 up into place creating a slight mechanical stop, resisting the lens 5 from sliding out of the groove 6.

Figure 5C:
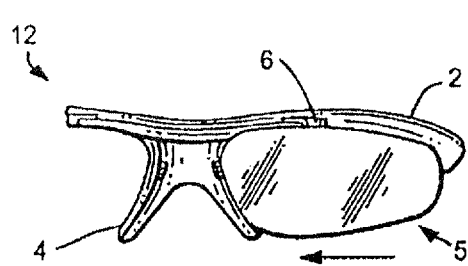

As seen in FIG. 5C, the lens 5 is positioned into a recess 6 of the upper rim portion 2 of frame 12 and slid towards the nosepiece 4. Once in this position, the attractive forces of the opposing magnets, positioned in the lens 5 and frame 12, secure the lens 5 to the frame 12. Additionally, the magnet in the lens 5 locks into the recess 6 and resists the lens 5 from dislodging out of the 'blade'-style frame 12.

Figure 5D:
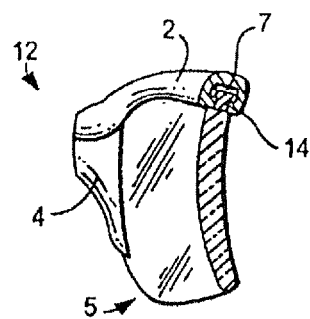
FIG. 5D is a cross-sectional view of a T-shaped magnetic attachment extending from the lens and received into a corresponding pocket of the frame, according to another embodiment of the present invention.

FIG. 5D shows another embodiment of the present invention. The lens 5 can comprise one magnet located at the portion of the lens 5 that attaches to the frame near the nasal area 4 and one mechanical "T" attachment 14 at the top. The frame 12 has magnets 7 positioned in the upper rim portion 2 of the frame 12 and the nosepiece 4.

Figure 6A:
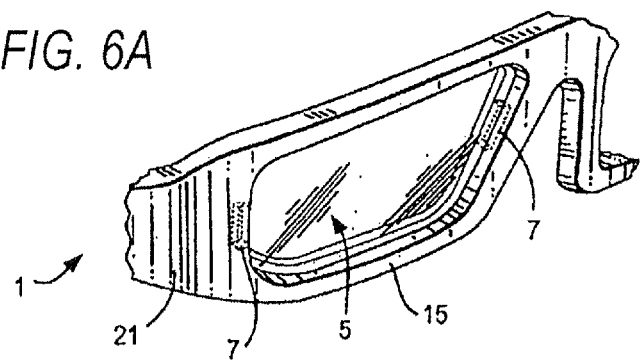
FIG. 6A is a perspective view of a pair of eyewear frames according to another embodiment of the invention.
Figure 6B:
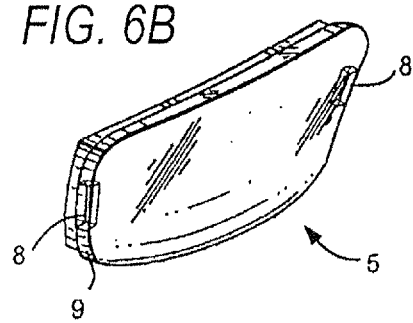
FIG. 6B is a perspective view of a lens according to an embodiment of the invention.
Figure 6C:
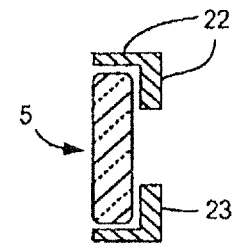
FIG. 6C is a cross-section of the frame and lens of the embodiment shown in FIG. 6A.

FIGS. 6A-6C show another embodiment of the present invention. The frame 1 may include a full rim 21 encompassing a lens 5. In this embodiment, the lens 5 must be inserted from either the front 15 or the back, as opposed to being slid into the frame 1 from the side as with the embodiment shown in FIGS. 1-3. In this embodiment of the present invention, the frame 1 does not have a channel-recess, but rather has a stepped interior surface 22 that provides a mechanical stop for the lens 5 when inserted, as shown in FIG. 6C. The step may be a raised back wall so that the lens may only be removed through the front of the frame. Alternatively, the step 23 may be a front wall so that the lens 5 may only be removed through the back of the frame 1. In such an embodiment, the lens 5, with embedded magnets 8 near the edge 9, is inserted into a frame 1 with a raised front or back wall and positioned so that the magnets 8 of the lens 5 align with the magnets 7 in the frame 1. The lenses 5 are inserted from the front or back accordingly, and are held into place by the magnetic force of the magnets on both the frame 1 and lenses 5.

Figure 7:
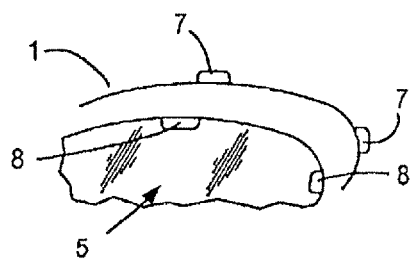
FIG. 7 is a front view of a partial eyewear frame having magnets glued into the rims according to all embodiments illustrated.

FIG. 7 shows another embodiment of the present invention. Similar to the previously described embodiments, the magnets 7 can be secured to the frame 1 of the eyeglasses. Magnets or magnetic material 8 are also secured to the lens 5. The magnets or magnetic material 7 secured to the frame 1 are embedded in a recess, so that they lie flush with the surface of the frame 1. This allows the magnets or magnetic material 7 secured to the frame 1 to attract the magnets or magnetic material secured to the lens 5, while allowing the lens 5 to fit flush to the frame 1.

Alternatively, the recess in the frame does not need to span the length of the horizontal arm. Magnets protruding from the edge of the lens, such as the magnets visible in FIG. 1D, could be received in one or more recesses in the horizontal arm of a frame. In such an embodiment, magnets or magnetic material, corresponding to the magnets or magnetic material protruding from the edge of the lens, could be secured inside of recesses in the horizontal arm of the frame that are contoured to fit the protrusions on the lens. The protrusions of the lens would then fit inside of these recesses in the horizontal arm of the frame.

Figure 8A:
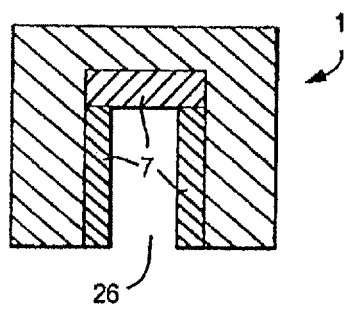
FIGS. 8A-8D are sectional views of magnets embedded in channels in the lens rims of frames in different embodiments of the present invention.
Figure 8B:
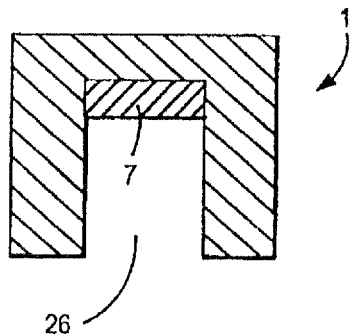
Figure 8C:
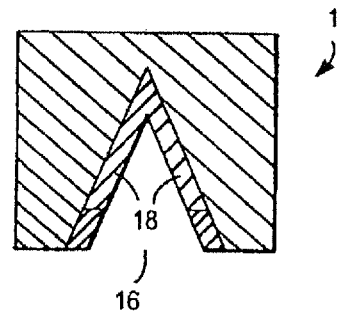
Figure 8D:
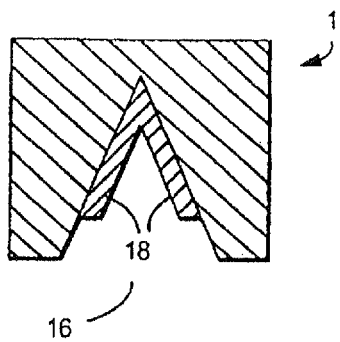

FIGS. 8a-8f show arrangements of magnets in the recesses of the frame. The recess can be of any shape. A recess having a square shape 26 and a recess having a triangular shape 16 are shown. In FIG. 8A, rectangular magnets 7 are positioned in a square-shaped recess 26 in a frame 1 so that a magnet is secured to each side of the recess. In FIG. 8B, a rectangular magnet 7 is positioned at the top of a square-shaped recess 26. Rectangular magnets need not be used. FIG. 8C shows a triangular-shaped magnet or magnets 18 secured to a frame having a triangular-shaped recess 16. FIG. 8D shows a triangular-shaped magnet 18 and recess 16 where the triangular shaped magnet 18 is not secured to all surfaces of the triangular-shaped recess 16.

Those skilled in the art will appreciate that there are many ways to configure the frame recesses in the rims to accept various types of lenses. There are even more possible ways to attach magnets to these different rim styles. The embodiments described are not intended to limit the combinations of magnetic placements and recesses in the rims. For example, those skilled in the art will appreciate that the horizontal arm of the frame could contain a protruding magnet or a protrusion with a magnet or magnetic material secured thereto and the lens may contain a recess with a magnet or magnetic material.

Figure 9A:
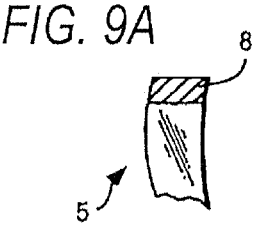
FIGS. 9A-9D are side views of magnets or magnetic material secured to various lenses.
Figure 9C:
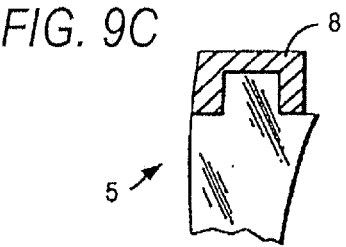
Figure 9B:
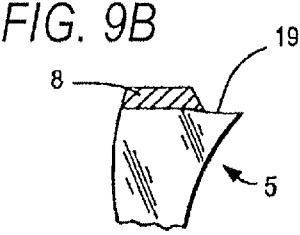
Figure 9D:
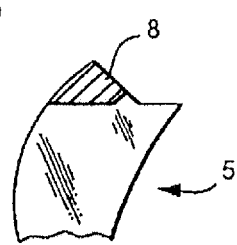

As illustrated in FIGS. 9A-9D, magnets can be secured to prescription or plano lenses. In FIG. 9A, the lens 5 and the magnet 8 are of equal thickness, however the magnets or magnetically attractive material secured to the lens may be thinner or thicker than the lens. Additionally, the magnets or magnetically attractive material may be a thin plate that is form-fitted into a shallow indentation in the edge of the lenses as shown in FIG. 9B.

It is also possible to press-fit the magnets 8 to lenses 5 having a notched surface, such as the lens 5 in FIG. 9C. The notched surface of the lens 5 is covered with a magnet that can be pressed over the lens 5 to create a corresponding surface for attaching the lens 5 to a frame. If desired, a magnet having a similar shape can be attached to a frame having a similar shape as this lens.

In an alternate embodiment, the magnet of FIG. 9C may be a moldable magnetic material overmolded onto at least a portion of the edge of a lens. As shown, the lens 5 may have a protrusion or tab extending in a radial direction from a portion of the edge of the lens. The protrusion or tab may extend around the entire perimeter of the lens or may extend from a portion or portions of the edge of the lens. Magnetic material 8 may be overmolded onto the protrusion or tab and may abut the edge of the lens as shown. The magnetic material may be overmolded such that the material is substantially flush with the front surface of the lens, the rear surface of the lens, or both the front and rear surfaces of the lens.

The notched surface of FIG. 9C may partially or completely extend around the perimeter of the lens 5.

In some embodiments of the invention, a lens 5 includes a lens cavity 43 at the edge 9 of the lens 5 such that the perimeter lens edge surface 9 is interrupted by a portion of the cavity 43 as shown in FIGS. 18A-18D. The cavity 43 may be formed when the lens is made or the cavity may be formed in the lens 5 at any other stage during the production of the lens. In any case, the lens edge surface 9 includes a localized discontinuity in the uniform configuration of the lens edge surface at the cavity.

According to some embodiments, the cavity has a proximal cavity portion 45, proximal to the circumferential lens edge surface 9, the proximal cavity portion having a first cavity dimension d1. The cavity according to some embodiments has a distal cavity portion 47 distal from the circumferential edge surface 9, the distal cavity portion having a second cavity dimension d2. In some embodiments, the second cavity dimension is greater than the first cavity dimension.

Figure 18A:
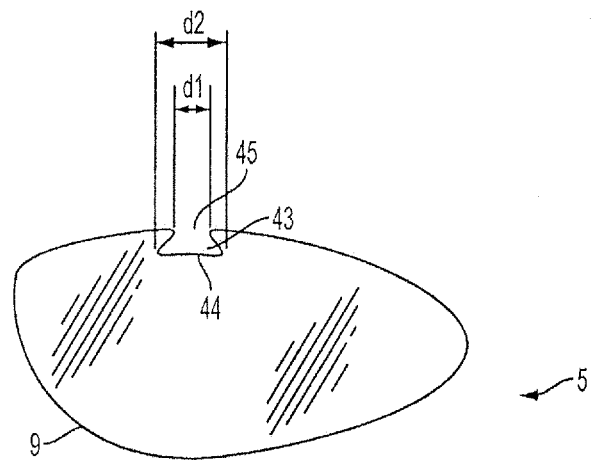
FIGS. 18A-18C are front views of various lens cavity shapes according to embodiments of this invention and FIG. 18D is a perspective view of lens cavity shapes according to embodiments of this invention.
Figure 19:
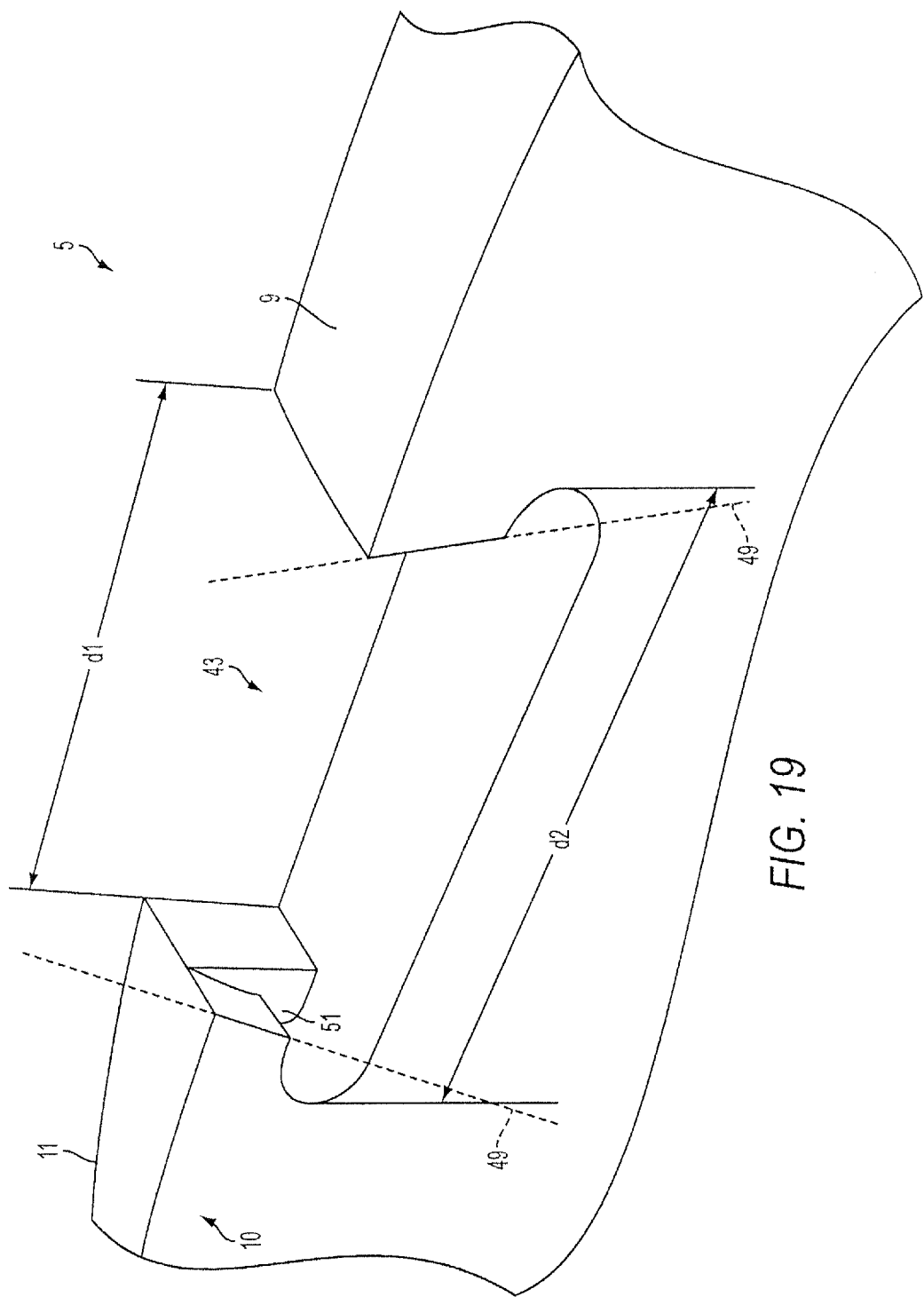
FIG. 19 is an enlarged perspective view of the cavity of FIG. 18A.

In some embodiments, the lens cavity 43 may be generally trapezoidal in shape with two substantially parallel opposing sides and two non-parallel sides as shown in FIGS. 18A and 19. According to some embodiments, at least one of the non-parallel sides may be inclined toward the other. As such, the cavity is generally shaped as the negative of a truncated triangular prism with a vertex formed by two sides truncated by a plane generally parallel to the third side. In FIG. 18A, a cavity with both non-parallel sides inclined toward each other with the extended inclined surface indicated in dashed lines 49.

In some embodiments in which the second lens cavity dimension is greater that the first lens cavity dimension, the lens cavity is the negative of a truncated isosceles triangular prism. In some embodiments, the lens cavity 43 is the negative of a truncated equilateral triangular prism.

The cavity 43 need not be the negative of a truncated triangular prism in order to have a second lens cavity dimension d2 that is greater that the first lens cavity dimension d1 to fall within the scope of this disclosure and the spirit of this invention. A consideration in choosing cavity shape is that the shape cooperates with a magnet or magnetic material (to be more fully disclosed below) placed within the cavity 43 to resist movement and separation or removal of the magnetic material from the lens cavity in a direction substantially perpendicular to the edge surface 9 of the lens in the area of the cavity 43.

Figure 18B:
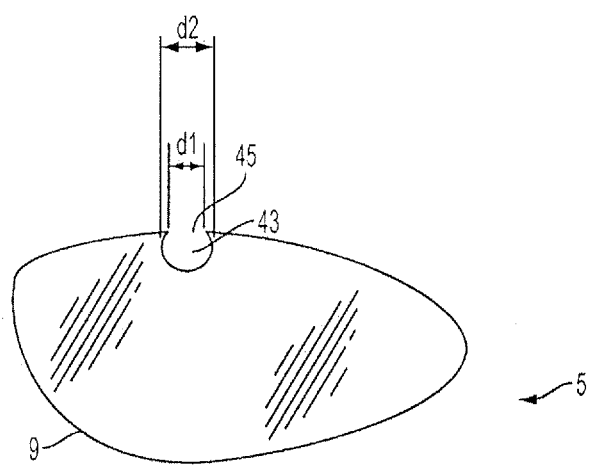

A non-limiting example of cavity shapes suitable for this invention includes a circular profile, truncated at a chord of the circle, such that the angular measure of the cavity is greater that 180° as shown in FIG. 18B. The chord length corresponds to the first cavity dimension.

Figure 18C:
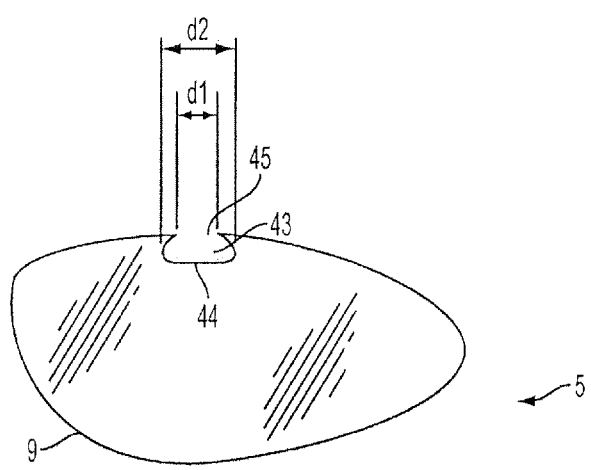

Another non-limiting example of a cavity shape suitable shape for this invention includes a generally truncated racetrack shape having semicircular ends connected by substantially straight and parallel segments as shown in FIG. 18C.

Figure 18D:
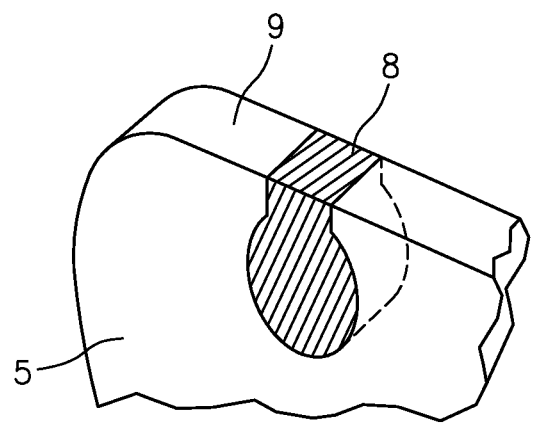

FIG. 18D illustrates a keyhole shaped lens cavity 43 which provides a second lens cavity dimension d2 that is greater that the first lens cavity dimension d1 to fall within the scope of this disclosure and the spirit of this invention. As illustrated in FIG. 18D, the lens cavity includes a substantially round portion distal from the edge of the lens and a linear portion having substantially parallel sides between the round portion and the edge of the lens. In other embodiments, the sides of the linear portion are not parallel and may converge or diverge toward the edge of the lens.

FIG. 18E illustrates a lens cavity 43 having a second lens cavity dimension d2 that is greater that the first lens cavity dimension d1. The lens cavity 43 is generally L-shaped in cross-section with the second lens cavity dimension d2 taken along the horizontal leg of the cross-section.

One of ordinary skill in the art would recognize many other suitable cavity shapes, in which the first cavity dimension is smaller than the second cavity dimension, which would be within the spirit of this invention.

The lens cavity 43 may extend from a front surface 10 of the lens to a rear surface of the lens 11, i.e., through the thickness of the lens. In some embodiments, the cavity may extend partially through the thickness of the lens. Other lens cavities according to this invention may have portions that extend through the lens thickness and a portion or portions that extend partially through the thickness of the lens as shown in FIG. 19.

In FIG. 19, cavity 43 has a central portion which extends from the front surface 10 to the rear surface 11. A portion of the cavity is obstructed by lens portion 51 which extends from the rear surface 11 of the lens 5 to a point located between the front and rear surfaces 10, 11 of the lens. Similarly, lens portion 51 could extend from the front surface 10 of the lens 5 to a point between the front and rear surfaces. FIG. 19 shows the surface 51 at the left side of the cavity as drawn. A lens portion similar to 51 may be found on the right side of the lens 5 as drawn (hidden in this view) in addition to, or in place of, the lens portion 51 on the left side.

Figure 21:
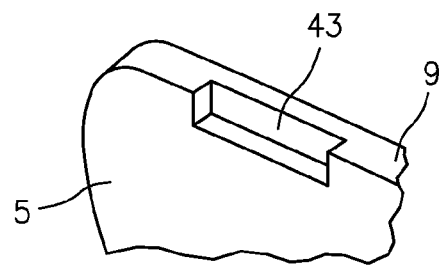
FIG. 21 is top view of a lens having a cavity of a certain shape on one side of the lens.
Figure 22:
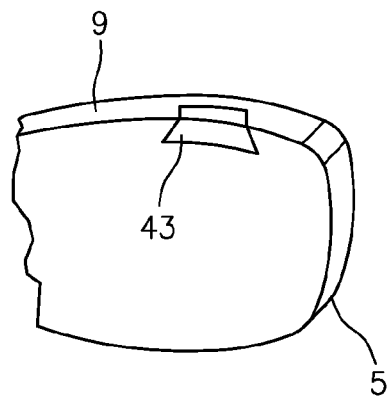
FIG. 22 is top view of a lens having a cavity of a certain shape on one side of the lens.
Figure 23:
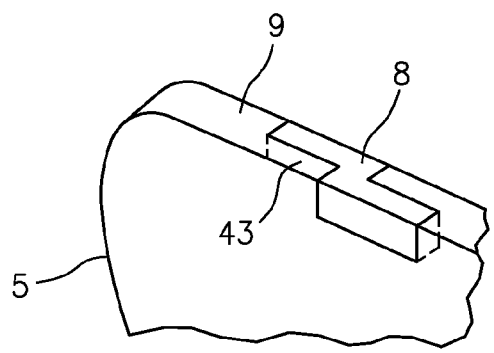
FIG. 23 is a top view of a lens having a cavity of a certain shape on the top edge of the lens and a magnet of a corresponding shape.
Figure 24:
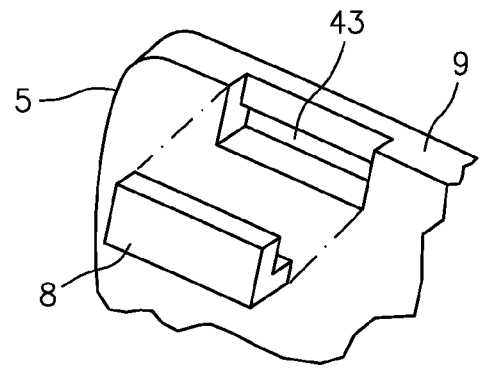
FIG. 24 is top view of a lens having a cavity of a certain shape on one side of the lens.

Other non-limiting embodiments in which a lens cavity extends only partially through the thickness of the lens can be illustrated in FIGS. 21-24. FIG. 21 illustrates a lens cavity 43 formed at the edge 9 of a lens. The cavity interrupts both the edge surface and one surface of the lens 5. An appropriately configured magnet may be fitted within the lens cavity using any known method. FIG. 22 is represents a trapezoidal cavity 43 extending partially through the thickness of the lens 5. FIG. 23 illustrates an offset lens cavity 43 and a suitably configured magnet fitted within the cavity. The lens cavity 43 illustrated in FIG. 24 is generally L-shaped in cross section with a vertical leg that extends through the edge 9 of the lens and a horizontal portion that partially or completely extends through the thickness of the lens.

When the lens magnet 8 in the non-limiting exemplary shapes of FIGS. 20A-20E of the present invention are combined with the appropriately shaped exemplary lens cavity of FIGS. 18A-18E, one or more surfaces of the lens magnet 8 may be flush with one or more surfaces of the lens 5. For example, in some embodiments, the lens magnet 8 and the lens 5 may be formed such that the edge surface of the lens magnet is flush with at least one lens edge surface 9 adjacent to the magnet 8. In other embodiments, a portion of a lens magnet surface may stand proud of an adjacent surface or surfaces of the lens or may be recessed from a surface or surfaces of the lens.

Figure 25C:
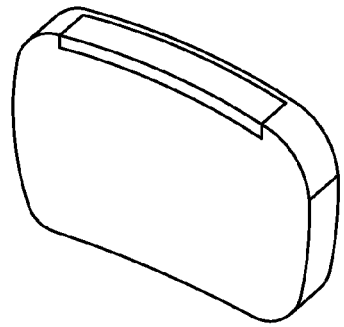
FIGS. 25A-D are perspective views of a lens having a cavity on one side of the lens running a substantial portion of length of the top edge of the lens and a magnet having a corresponding shape.
Figure 25A:
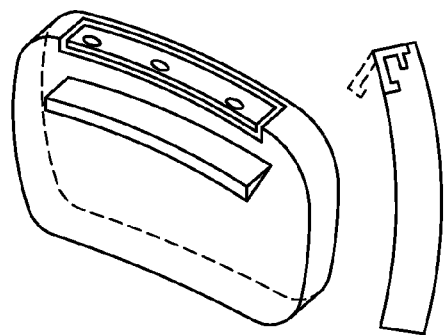
Figure 25B:
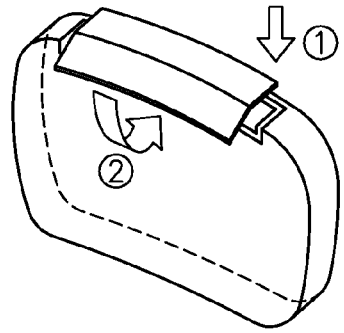

FIGS. 25A-25D illustrate an embodiment in which a recess is cut on both an edge 9 and a front 10 (or rear 11) surface of the lens 5. As shown in FIGS. 25a-c, a recess is cut on the rear surface 11 of the lens 5 and an edge 9 of the lens, but does not go through to the front surface 10 of the lens. In some embodiments, the edge recess may go through a portion of the front lens surface. Additionally, the lens recess may include details such a holes, formed in the lens, generally perpendicular to the lens surface 11 and edge 9. The details may be, for example, cylindrical or conical holes, notches, undercuts or the like, positioned to engage corresponding cylindrical or conical bosses, ribs, or protrusions on the magnetic material 8 to secure the magnet material 8 to the lens 5.

Figure 25D:
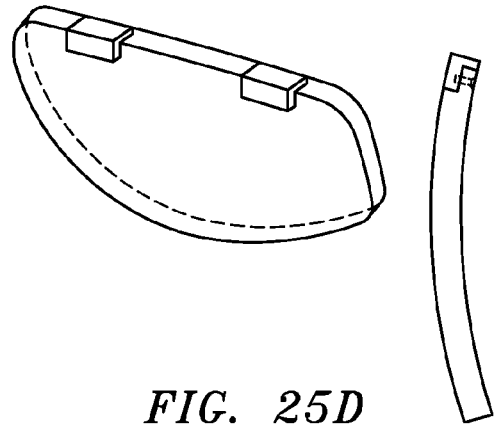

FIG. 25D illustrates a recess cut on both an edge 9 and a front 10 surface of the lens 5 in which a portion of the recess on the edge 9 of the lens is cut through from the front surface 10 to the rear surface 11 of the lens 5. A mechanical fastener may be used to secure the magnet to the lens with or without the use of adhesive, or adhesive along may be used. A similar embodiment has the recess as illustrated starting at the rear surface 11 and extending to the front surface. The magnet may be substantially flush with the adjacent edge of the lens or may be recessed from the edge or stand proud of the edge.

Figure 26:
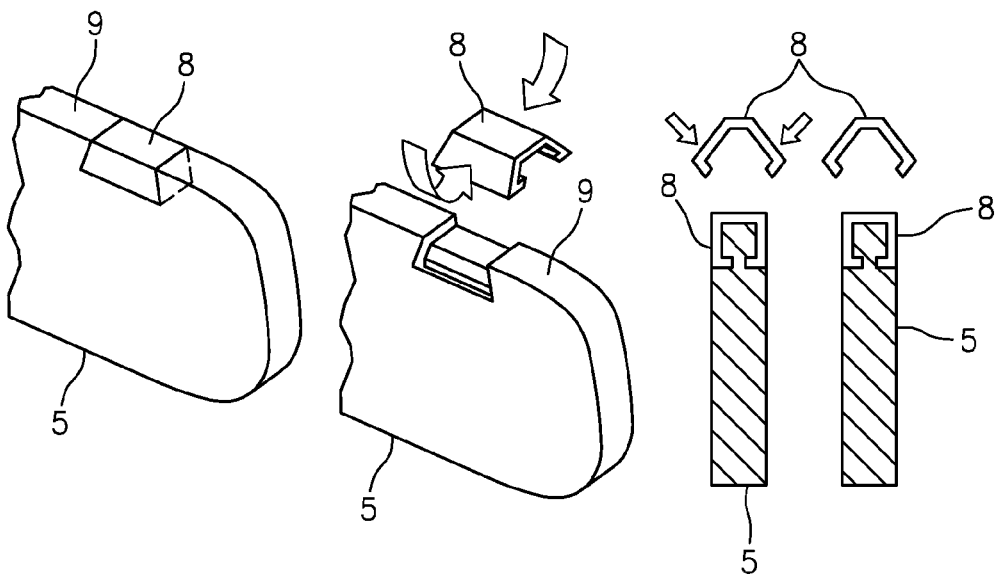
FIG. 26 is a top view of a lens having a cavity of a certain shape on the top edge of the lens and a magnet of a corresponding shape.

Similarly, FIG. 26 illustrates a magnetic material 8, formed with details to correspond with at least a portion of the edge 9 of the lens 5, and deformable to securely engage the lens. For example, the edge of the lens may be formed similar to a portion of a dovetail configuration and the magnetic material formed in a cooperating configuration, with portions of the magnetic material displaced to allow the magnetic material to accept at least a portion of the lens. The magnetic material may then be deformed to assume a closely fitting cooperating dovetail configuration and engage a portion of the lens. Other details on the magnetic material and lens edge may be used with similar results.

Figure 27:
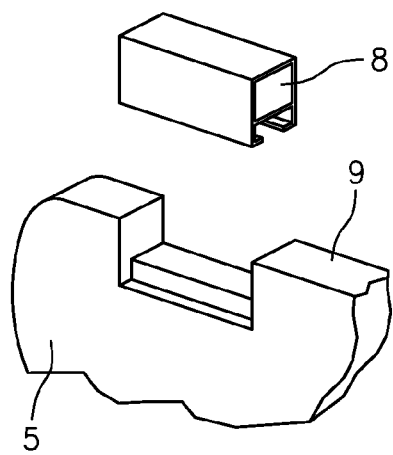
FIG. 27 is a top view of a lens having a cavity of a certain shape on the top edge of the lens and a magnet of a corresponding shape.

FIG. 27 illustrates an embodiment in which a magnetic material 8 may be accepted within a deformable clip or retainer. The retainer may be deformed to a configuration in which details on the clip cooperate with details on the lens 5 to secure the magnetic material to the lens. The clip may be a magnetic material or a non-magnetic material.

Figure 28A:
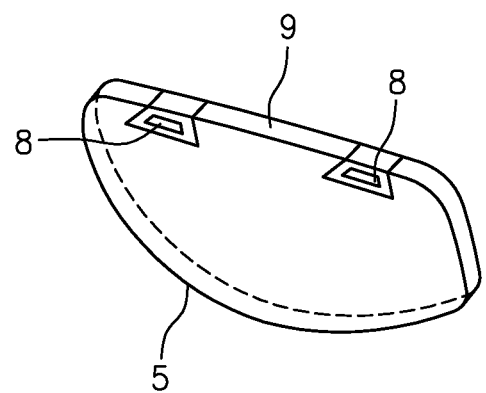
FIGS. 28A-C is a top view of a lens having cavities of a certain shape on the corners of the lens and magnets of a corresponding shape.

In alternate embodiments, a magnetic material may be placed within a carrier and the carrier fitted to any of the lens cavities presented above. For example, in FIG. 28A, a generally rectangular magnet 8 is fitted within a carrier, illustrated as trapezoidal in shape, adapted to be received within a lens cavity. The carrier may be fixed within the lens cavity using any technique known to the art, for example, press fit or with mechanical fasteners or adhesive. Similarly, the magnetic material may be secured to the carrier with any known method as above. When assembled, the carrier may or may not be flush with the edge 9 of the lens 5.

Figure 28B:
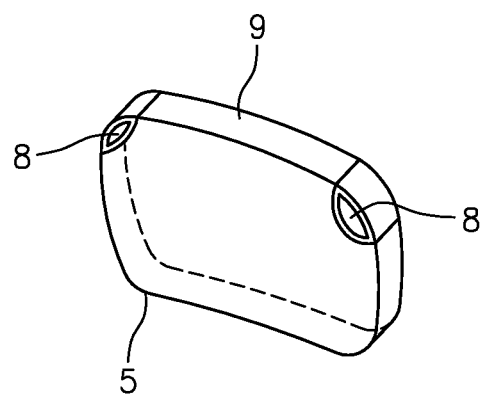
Figure 28C:
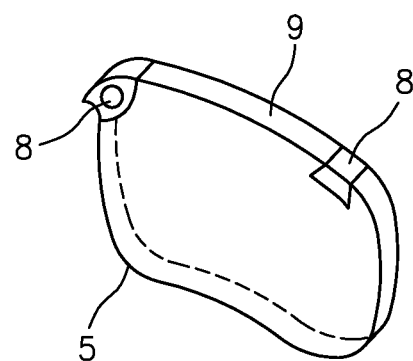

FIGS. 28B and 28C illustrate magnetic materials placed in one or more of the general corner areas of the lens, the corners being generally the areas in which the top edge of the lens transitions to a side of the lens as would generally be recognized in the figures. The embodiment of FIG. 28B includes carriers placed at the corners, the carriers accepting magnetic materials within an internal section of the carrier. The embodiment of FIG. 28C includes a carrier at the corner of the lens as in FIG. 28B, the carrier including a hook-shaped projection to engage a portion of the frame as well as retaining a magnetic material. The lens may include additional magnetic materials, mounted with or without carriers.

Magnets can be positioned on any side of the frame or recess and can be of any suitable shape. Magnets 8 can be attached to lenses having arcuate surfaces, such as the lens 5 in FIG. 9A. Magnets can also be attached to lenses having notches 19 that project away from the arcuate surface, such as the lens 5 in FIG. 9B. In either respect, the magnets are attached to the substantially arcuate portions of the lenses, not the notched portions. There is preferably a first magnet attached to the upper surface of the frame and a second magnet attached to the interim surface, close to the nosepiece. More than one magnet can be attached to either the lens or the frame.

Figure 10A:
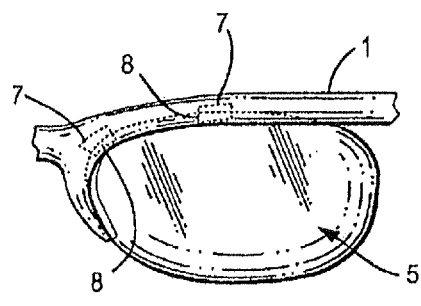
FIGS. 10A-10B are front views of an embodiment of the present invention in a blade-style frame.

FIG. 10A shows a front view of another embodiment of the present invention. A lens 5 is secured to a frame 1. Magnets or magnetic material 8 secured to the lens 5 attracts magnets or magnetic material 7 secured to the frame 1. The magnets or magnetic material 7 secured to the frame 1 are recessed in a channel in the frame 1 so that the magnets or magnetic material lie flush with the surface of the frame 1 and the top of the lens 5.

Figure 10B:
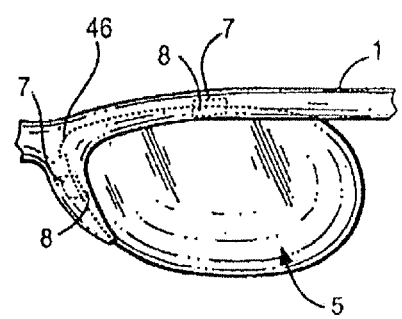

FIG. 10B shows a front view of another embodiment of the present invention. A lens 5 is secured to a frame 1. Magnets or magnetic material 8 secured to the lens 5 attracts magnets or magnetic material 7 secured to the frame 1. The magnets or magnetic material 7 secured to the frame 1 are recessed in a channel in the frame 1 so that the magnets lie flush with the surface of the frame 1 and the top of the lens 5. A notch 46 cut in the lens 5 is received in a similarly shaped recess in the frame 1 and assists in securing the lens 5 to the frame 1.

Figure 11A:
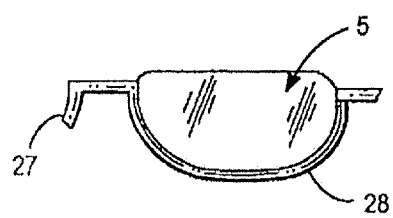
FIG. 11A is a front view of a semi-rimmed frame embodiment of the present invention.

Another type of eyeglass frame that benefits from attaching magnetic lenses 5 to a frame having magnetic surfaces is the semi-rimmed frame 27, as illustrated in FIGS. 11A-11E. The frames 27 are typically metal rims 28 with substantially arcuate surfaces corresponding to the lower halves of the lenses 5, as seen in FIG. 11A. Only the lower portions of the lenses 5 and parts of the sides of the lenses 5 are covered by the frame 27. The remainder of the lens 5, the upper substantially arcuate surface, is rimless. Those skilled in the art will understand that this embodiment is not only limited to the lower portion of the lens being covered by the frame, but may include other partial sections of the lens, such as the top half of the lens covered by frame.

Figure 11B:
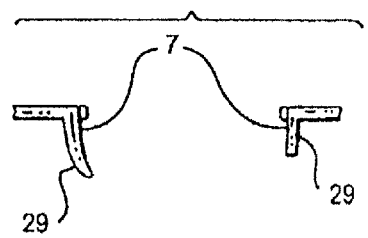
FIG. 11B is a side view of portions of a partial rim, which were shown in FIG. 11A, according to another embodiment of the present invention.
Figure 11C:
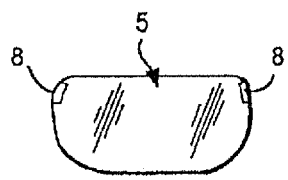
FIG. 11C is a front view of a lens, which was shown in FIG. 11A, according to another embodiment of the present invention.
Figure 11D:
FIG. 11D is a side view of a lens, as shown in FIG. 11C, according to an embodiment of the present invention.
Figure 11E:
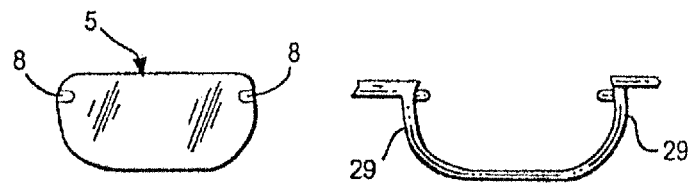
FIG. 11E is a front view of a lens and partial rim, which were shown in FIG. 11A, according to another embodiment of the present invention.

To secure lenses 5 in semi-rim frames 27, magnets 7 are embedded in the side surfaces 29 of the rims 28, towards the corners of the lenses 5, as shown in FIGS. 11B and 11C. Persons of skill in the art will appreciate that the lens 5 could similarly be attached to the semi-rimmed frame by embedding magnets in the portion of the rim 28 encompassing the bottom surfaces of the lenses 5 and securing corresponding magnets 8 in the bottom portion of the lenses 5. Magnets, or magnetic material, 8 are attached to the edges 9 of the lenses 5, as shown in FIG. 11C, to match the corresponding bevel of the frame, as shown in FIG. 11B (square groove, substantially v-shaped groove, or round wire). This allows for a close fit between the magnetic lens 5 and the magnets or magnetic material 7 of the frames 27. The metal or molded wire of the eyeglass frames 27 is typically constructed from a square groove, a substantially v-shaped groove, or a round wire, also illustrated in FIG. 11B. FIG. 11E shows a front view of the lens and the semi-rimmed frame of FIG. 11A disassembled.

Figure 12A:
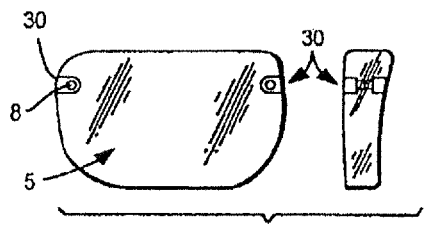
FIGS. 12A, 12A', 12B, 12C and 12C' show a three-piece-mount embodiment of the present invention.
Figure 12A:
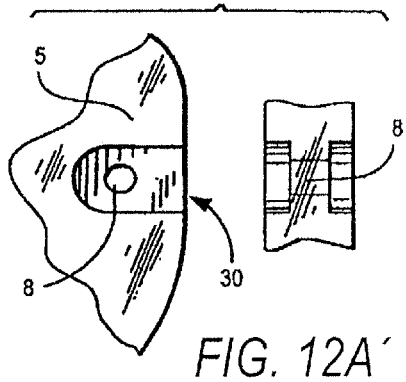
Figure 12B:
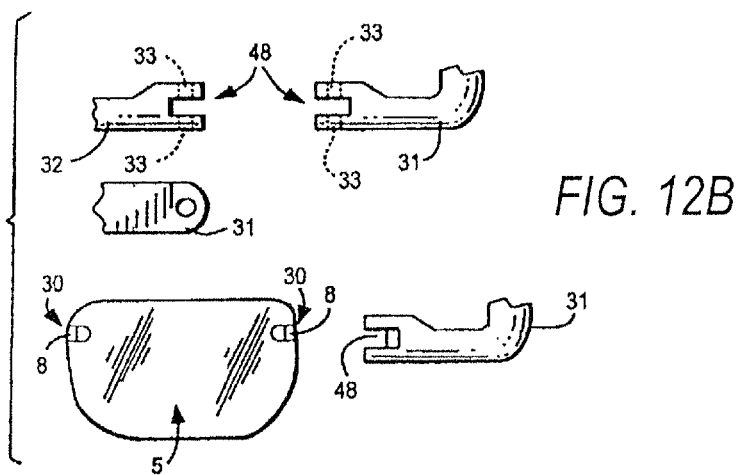
Figure 12C:
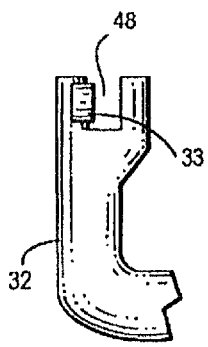
Figure 12C:
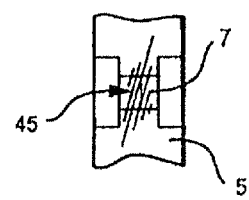

In yet another embodiment of the present invention, another type of magnetic attachment, illustrated in FIGS. 12A-12C', is associated with the three-piece mount, also referred to as a rimless mount. The three-piece mount involves a frame constructed without rims or eye wires. The three-piece mount has three pieces: the bridge bar 32, the temple or endpieces 31, and the lenses 5. Rimless mounts typically include two lenses 5 connected with a bridge bar 32 that attaches to the inner edge of the lenses 5, and temple or endpieces 31 that are attached to the outer edge of the lenses 5. The magnets in a three-piece mount link the three pieces to each other. The bridge bar 32 connects to the inner corners and/or edges of the lenses 5, and the temple or endpieces 31 connect to the outer corners or edges of the lenses 5.

The magnets 8 secured to the lenses 5 in the three-piece mount embodiment shown in FIGS. 12A-12B are attached to areas of each lens 5 defined by first and second indentations, collectively 30, on the front and rear surfaces at the inner and outer corners of the lenses 5. The magnets 8 are located directly between the first and second indentations, towards the inner and outer layers of the lens, as seen in FIGS. 12A and 12B, so as to attract the magnetic surfaces 7 of the frame pieces.

The preferred method of attaching the lenses 5 to the bridge bar 32 is illustrated in FIG. 12B, where the magnets secured to the bridge bar 33 are located in the slot 48 of the bridge bar 32, furthest from the edge of the bridge bar 32. This slot 48 will preferably be closest to the inner corners of the lenses 5 when the forces of the magnets in the bridge bar 33 pull the opposing magnets in the inner corners of the lenses 8 towards the bridge bar magnets 33. The attractive forces of the magnets increase when the magnets are close to each other and prevent the three-piece mount from unlinking.

In another embodiment of the three-piece mount, the lenses 5 can be encompassed by metal around the edge of the lens, with at least one magnet located in the bridge bar 32 only. In such an embodiment, there is no need for magnetic members in the temple pieces. In another embodiment, the bridge bar 32 can be metal with at least one magnet secured to the lens 5.

As illustrated in FIG. 12C, each temple or endpiece and bridge bar 32, includes a magnet or magnetic material 33, on a first end, closest to the outer corner or edge of each lens 5. The magnets attached to the temple or endpieces 31 or bridge bar 32 protrude towards the outer corners of the lenses 5 for attracting the corresponding magnets embedded in the lenses 5. This reaction is similar to the reaction between the magnets in the bridge bar and the magnets at the inner corners of the lenses 5. This variation can also be achieved in the opposite direction, with the magnet or protrusion in the rear of the lens 5.

As seen in FIG. 12B, it is possible for the magnets or magnetic material 33 in the temple endpieces 31 to be positioned at the base of the endpieces 31, towards the furthest end of the slot 48 with respect to the lenses 5. Lenses 5 have magnets 8 attached to the outermost edge of the recess towards the endpiece. Upon insertion of lenses into endpieces, magnets 8 and 33 pull themselves together, securing lenses 5 into endpieces 31. A complimentary configuration can be at the bridge and lens locations, 32 and 30. In other words, the magnets 33 are positioned on either the upper or lower portion of the recess, towards the first end, closest to the lenses 5.

Figure 13:
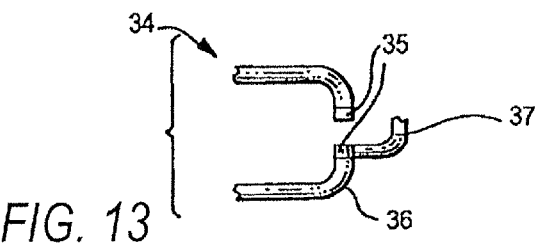
FIG. 13 is a front view of a magnetic rimlock closure embodiment of the present invention.

Another embodiment of the invention is a magnetic rimlock closure, illustrated in FIG. 13. In this attachment method, magnets 35 are secured to the rims 36 of the frames 34 in the distal corners, at the side opposite the brow bar. Specifically, the magnets are attached at the site where the frames 34 are generally locked—the rimlock. This is also the location where the temple pieces 37 are connected to the rims 36. In the present invention, the magnet replaces the screw as the locking feature. In a conventional rimlock, as in the present invention, the upper and lower sections of the frame separate at the temple corners. In a conventional rimlock, a screw connects the upper and lower sections. At the junction of the upper and lower sections of the frame, the magnets 35 are applied to the ends of the frames 34. The magnetic rimlock eliminates the need for a screw to lock the frames 34 at this junction because the magnetic forces secure the ends of the frame. Since the magnets 35 are attached to both ends of the frame, it is possible to use this magnetic rimlock method with frames of any suitable shape, including, but not limited to, a round or v-shaped eye wire. In this embodiment, it is not necessary that the lenses have magnets embedded therein. The lenses may be received in a recess in the rims of the frames 34 and held securely in place upon the closing and magnetic locking of the rimlock. Persons of skill in the art will appreciate that the rimlock can also be at the nasal bridge portion of the frame and not only at the temple or endpiece portion of the frame.

Figure 14A:
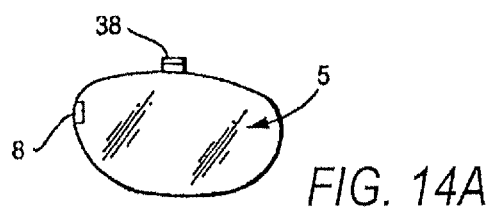
FIGS. 14A-14C are front and side views of an embodiment of the present invention with a slide pin.
Figure 14B:
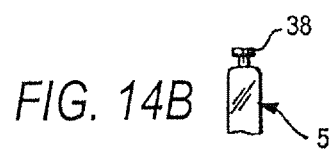
Figure 14C:
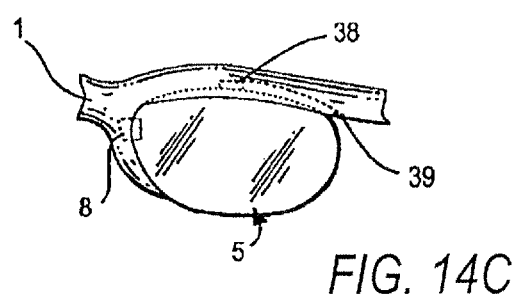

Another embodiment of the magnetic attachment method of the present invention is the combination of a magnet with a non-magnetic pin 38 as illustrated in FIGS. 14a-c. It is possible to attach a non-magnetic pin 38 to the upper substantially arcuate surface of the lens, as seen in FIG. 14A. This pin 38 would be received in a frame 1 having a slot 39 or channel, such as the frame 1 in FIG. 14C. The lens 5 is supplied with a magnet 8 on its inner surface, closest to the brow bar, for coupling to a magnet embedded in the frame 1. The lens 5 is also secured to the frame 1 with a slide pin 38, as seen in FIG. 14C, which moves into a slot 39 in the frame 1 for securing the lens 5. The pin 38 can be a substantially T-shaped pin that would lock into place when the lens 5 is positioned into the frame 1.

Figure 15A:
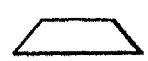
FIGS. 15A-15H are front and side/sectional views of the various shapes of magnets possible with the various methods of attachment.
Figure 15B:
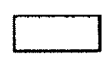
Figure 15C:
Figure 15D:
Figure 15E:
Figure 15F:
Figure 15G:

The magnets or magnetically attractive material described in the above methods of attachment can be formed of any suitable magnetic material known in the art and may be contoured and shaped in any manner. The magnets are typically lightweight so as not to burden the user with heavy frames. As seen in FIGS. 15A-15H, the magnets can be any shape, including, but not limited to, trapezoid (FIG. 15A), rectangle (FIG. 15B), round (FIG. 15C), crescent (FIG. 15D), square (FIG. 15E), v-shape (FIG. 15F), and triangle (FIG. 15G).

In all of the described embodiments, the magnets or magnetically attractive material may be embedded into the lenses and the frames, glued into the lenses or the frames, pressed and expansion-fit into the lenses and the frames, or fitted into the lenses and frames by any other suitable method.

Figure 15H:

Further, turning to FIG. 15H, the magnets can be received by channels, or recesses, for coupling to opposing magnetic surfaces. It is also possible to use the magnets as surfaces for restrictive substances, such as glue, so the magnet can be secured to lenses or frames.

FIG. 16A shows the present invention in a goggle embodiment. Magnets or elements of magnetic material 8 are secured to a shield-style lens 40 suitable for mounting in a goggle-style frame 41. Oppositely charged magnets or magnetic material 7 are secured to the goggle-style frame 41. The oppositely charged magnets or magnetic material 7 in the goggle-style frame 41 are placed so that the magnets or magnetic material 8 in the shield-style lenses align with the magnets 7 in the frame 41 when the lens 40 is mounted to the frame 41. The attractive forces between the magnets or the magnets and magnetic material couple the lens to the frame. Those skilled in the art will appreciate that securing the magnets 7 in a groove or recess 6 in the frame 41 will assist in securing a lens to the frame 41. The groove or recess 6 may be sized to securely accept the lens thereby holding it in place, as shown in FIG. 16B. FIG. 16B shows a cross-section of a goggle frame with double-lenses mounted in the frame.

While FIG. 16A shows magnets or magnetic material 8 secured to the sides of the shield-style lens 40, those skilled in the art will appreciate that magnets or magnetic material could be secured to any portion of a shield-style lens 40 as long as the magnets or magnetic material secured to the lens correspond in location to magnets or magnetic material secured to the frame. Those skilled in the art will also appreciate that lens styles other than shield-style lenses may be secured to a goggle-style frame through the use of magnets in accordance with the present invention. An example of such a lens style is shown in FIG. 16C. Those skilled in the art will also appreciate that one lens of any style may be permanently attached to the frame with or without magnets while a second lens of any style may be releaseably attached to the same frame using magnets according to the present invention. It may be desirable to combine shield-style lenses with conventionally shaped lenses in a goggle style frame.

Figure 17A:
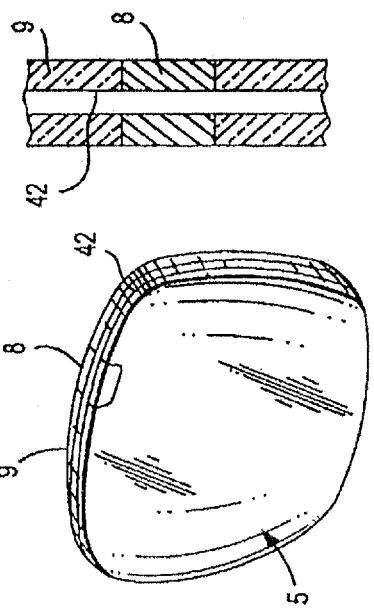
FIG. 17A is a front view of a lens with a wire surrounding its edge.
Figure 17B:
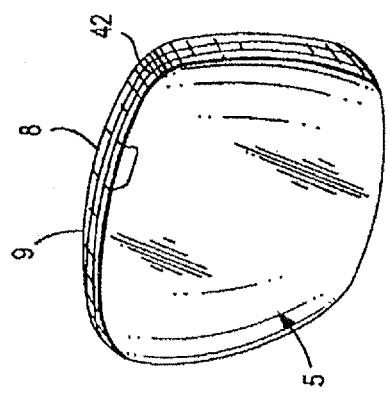
FIG. 17B is a front view of a lens with a wire surrounding its edge and a magnet or magnetic material embedded in the lens.
Figure 17C:
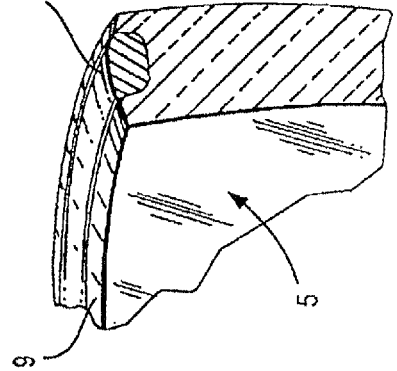
FIG. 17C is a perspective view of a wire partially embedded in a groove in the edge of a lens.
Figure 17D:
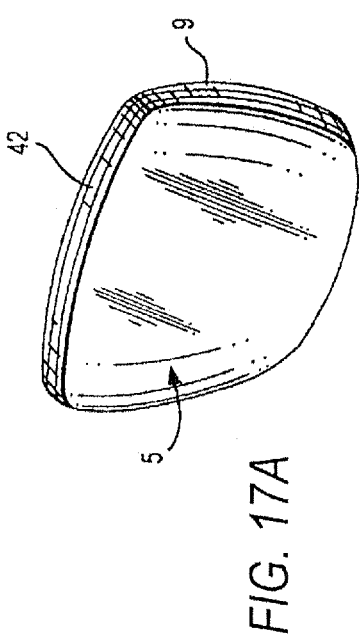
FIG. 17D is a top view of the lens in FIG. 17B.

FIG. 17A shows another embodiment of the present invention. A lens 5 is surrounded by a wire 42 on the edge 9 of the lens 5. A wire 42 may also be used as magnetic material so that coupling the lens to the frame may be accomplished by securing at least one magnet to the frame and no magnets to the lens. In an alternative embodiment, a wire 42 may also wrap over the top of a magnetic member to secure the magnetic member 8 to the lens 5, as shown in FIGS. 17B and 17D. FIG. 17B shows another embodiment of the present invention. A wire 42 surrounds a lens 5. A magnet or magnetic material 8 is embedded in the lens 5. Oppositely charged magnets or magnetic material are secured to the frame that the lens is to be mounted to. The oppositely charged magnets in the frame should be placed so that the magnets or magnetic material 8 in the lens align with the magnets in the frame when the lens is mounted to the frame. The attractive forces between the magnets or the magnets and magnetic material couple the lens to the frame. Those skilled in the art will appreciate that a wire 42 may also be embedded in a groove in the lens as shown in FIG. 17C. Those skilled in the art will also appreciate that a wire may also be used to snap into the frame to assist the magnetic attractive forces in securing the lens to the frame.

In some embodiments of the present invention, lens magnets or magnetic material 8 may be shaped to cooperate with the cavity 43 to provide some mechanical retentive force to resist edgewise removal of the magnet 8 from the cavity 43. Edgewise removal of the magnet 8 as used in this disclosure refers to the removal of the magnet 8 from the cavity 43 in a direction substantially perpendicular to the edge surface 9 of the lens in the area of the cavity. An ordinarily skilled artisan would appreciate that many cavity/magnet shapes would provide such cooperation. The non-limiting examples provided in FIGS. 18A-18C for the cavities and 20A-20C for the magnet shapes are provided merely for illustration and not for limitation of the present disclosure.

Figure 20A:
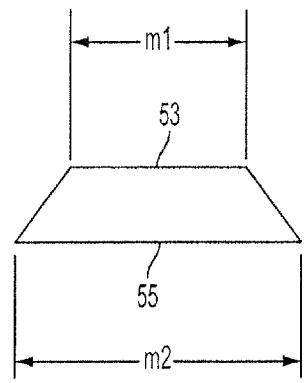
FIGS. 20A-20D are front views and FIG. 20E is a perspective view of the various magnet shapes corresponding to the lens cavity shapes shown in FIGS. 18A-18E.
Figure 20B:
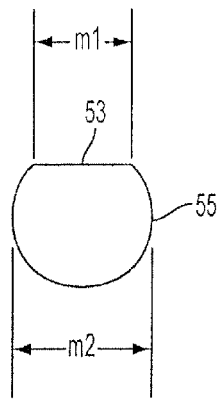
Figure 20C:
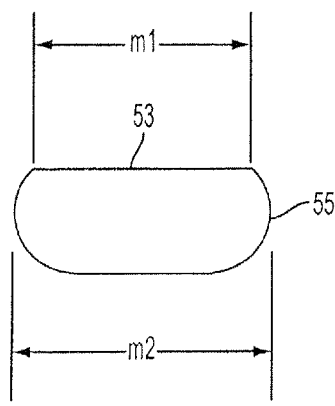
Figure 20D:
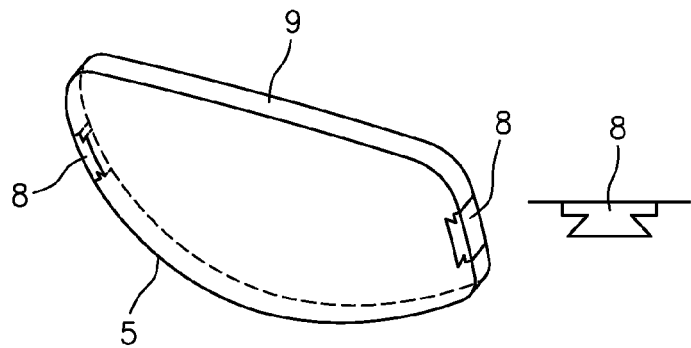
Figure 20F:
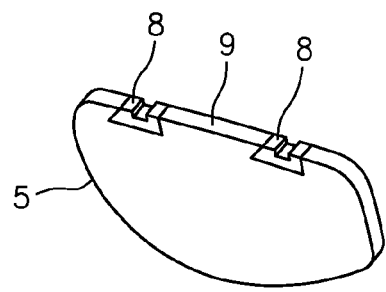
FIGS. 20F-G is a top view of a pair of lenses having a cavity of a certain shape and magnets with corresponding shapes.
Figure 20E:
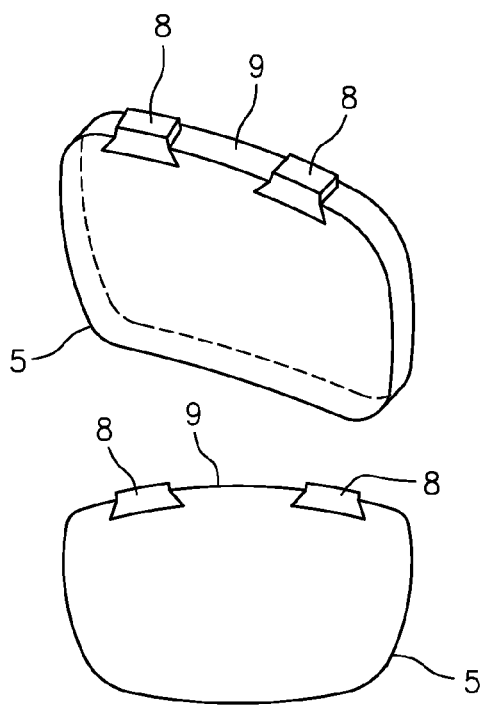
Figure 20G:
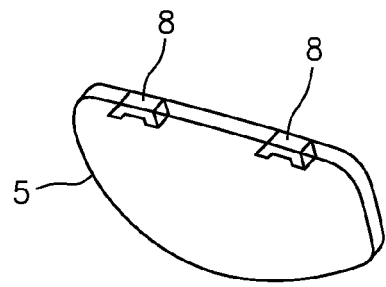

As shown in FIGS. 20A-20G, lens magnets 8 may have a first magnet portion 53 with a first magnet dimension m1, and a second magnet portion 55 with a second magnet dimension m2 that is larger than the first magnet dimension m1. FIG. 20E illustrates a lens magnet having first and second magnet portions 53 and 55, with an additional portion of the magnet adapted to extend beyond the edge of the lens as shown.

In the non-limiting, illustrative cavity/magnet pairs (18A/20A through 18C/20C), the cavity and magnet are formed to facilitate placement of the magnet into the cavity from the front surface 10 or the rear surface 11 of the lens 5, or in some case either from the front or the rear surface. The cavity 43 and magnet 8 are also shaped to prevent or at least substantially prevent passage of the magnet 8 into, or out of, the cavity 43 through the proximal portion of the cavity 45 at the lens edge 9. In some embodiments, this relationship can be achieved by providing a cavity 43 with a second cavity dimension d2 that is larger than the first cavity dimension d1 and providing a magnet 8 having a second magnet dimension m2 configured to closely fit within d2 and a first magnet dimension m1, smaller than m1, configured to closely fit within d1. Suitable selected cavity/magnet pairs cooperate mechanically to resist at least the edgewise movement with respect to the edge of the lens 5.

Embodiments of the present invention may include a band or strip of material on the edge 9 of the lens 5. The strip of material may be a magnetic material suitable for use with magnets located in the frame or the strip may be non-magnetic material, the function of which may include securing magnetic materials to the lens 5.

For example, FIGS. 29A and 29B illustrate a strip of material fitted within a groove or channel formed on the edge of the lens 5. The groove may fully or partially encircle the lens and the material may be at least partially placed within the groove.

FIGS. 30A and 30B illustrate an embodiment in which the strip of material has a general C-shape and accepts the edge of the lens within the opening of the C. A portion of the strip covers at least a portion of the edge of the lens and may cover a portion of the front surface of the lens or the rear surface of the lens, or both the front and rear surfaces of the lens.

Figure 31A:
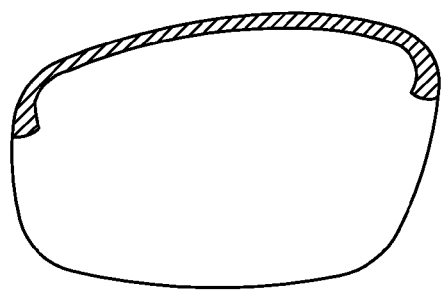
FIGS. 31A-E is top view of lenses having a cavity of a certain shape running along the length of the top edge of the lenses and magnets of a corresponding shape.

FIG. 31A illustrates a strip of material affixed to an edge portion of a lens 5. The strip of material has projections on its ends configured to engage undercuts on edge surfaces of the lens to secure the strips to the lens. The strip may be magnetic material or non-magnetic material and may secure magnetic material or materials to the edge of the lens.

Figure 31B:
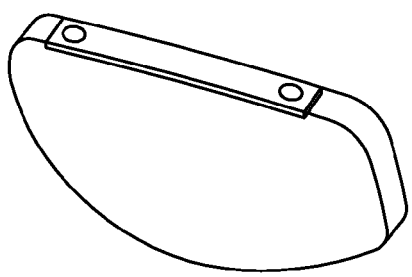

FIG. 31B, similar to FIG. 31A, illustrates an embodiment including a strip of material affixed to an edge of the lens with mechanical fasteners and/or adhesive. Cooperating details on the lens and the strip of material may be included to provide a measure of attachment for the material to the lens.

Figure 31C:
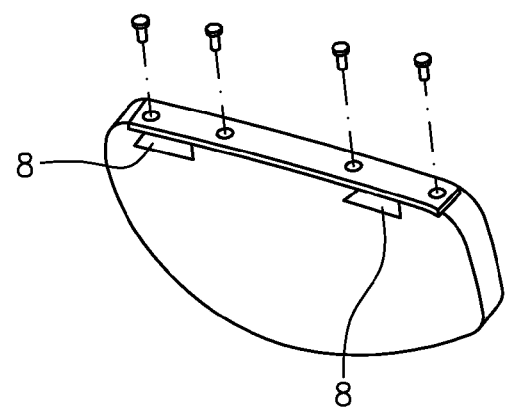

An alternate embodiment is illustrated in FIG. 31C in which a strip of material is affixed to an edge of a lens 5 with mechanical fasteners and/or adhesive and secures magnetic materials within a lens cavity or cavities. The strip of material and the magnetic materials may be formed from the same material or different materials.

Figure 31D:
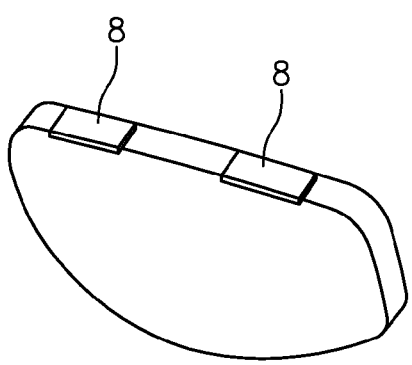
Figure 31E:
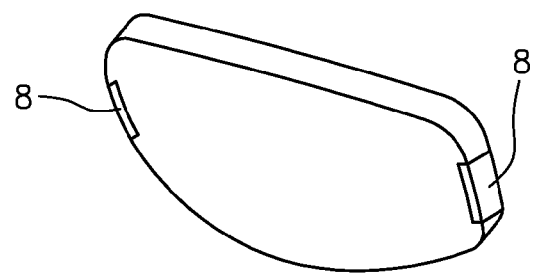

FIGS. 31A-31C illustrate the strip of material as primarily affixed to a long edge of the lens, specifically the top edge. However, similar strips of material may be placed anywhere around the perimeter of the lens and may be longer or shorter than the strips illustrated as required. FIGS. 31D and 31E provide non-limiting examples of shorter length strips placed on edges other than the top edge. The strips may be secured with mechanical fasteners and/or adhesive.

In other embodiments, magnets or magnetic materials may be placed in pockets formed at or near to the perimeter of the lens. FIGS. 32A-32G illustrate non-limiting examples of pocket shapes according to embodiments of the invention. As illustrated, the pockets may be formed in the edge of the lens with suitably shaped magnets or magnetic material fitted to the pockets.

Figure 33A:
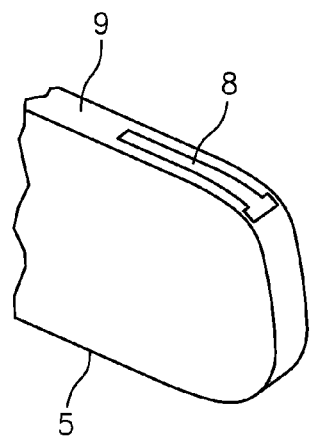
FIGS. 33A-33D is top view of lenses having a cavity of a certain shape running along the top edge of the lens and magnets of a corresponding shape.
Figure 33B:
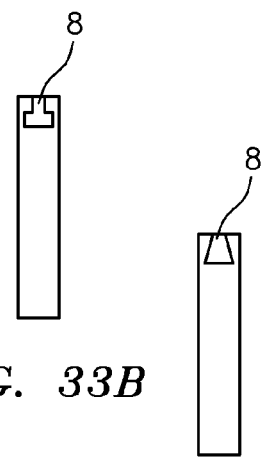
Figure 33C:
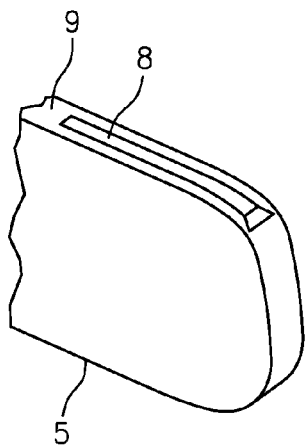
Figure 33D:
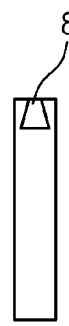

FIGS. 33A-33C illustrate pockets formed as channels in the edge of the lens and oriented generally parallel to the front and or rear surface of the lens. As illustrated in FIGS. 33B and 33D, exemplary cross-sectional shapes of the channels shown in FIGS. 33A and 33C, respectively, include an inverted T-shape or a truncated triangle with the truncated corner facing outward from the edge of the lens.

Figure 34:
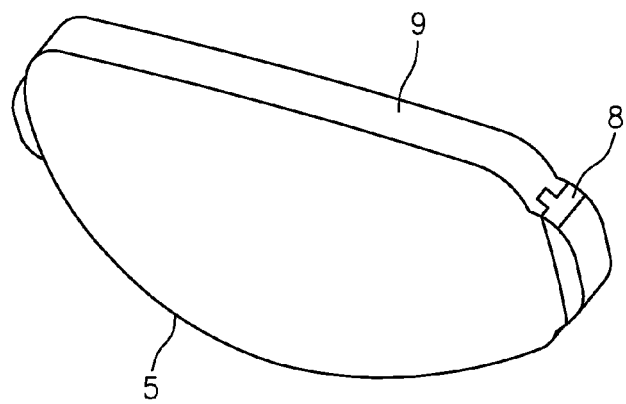
FIG. 34 is a perceptive view of a lens with cavities of a certain shape on the side edge of the lens and a magnet of a corresponding shape.

An alternate embodiment is illustrated in FIG. 34 in which a pocket formed as a channel as in FIGS. 33A-33C is provided in a portion of the lens perimeter that projects outward from the edge of the lens. A portion of the magnet or magnetic material is configured to be accepted in the channel.

Figure 35A:
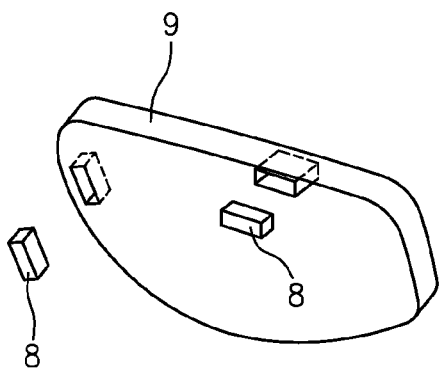
FIGS. 35A-C is a perceptive view of lenses with cavities of certain shapes running through the front and back faces of the lenses and magnets of corresponding shapes.
Figure 35B:
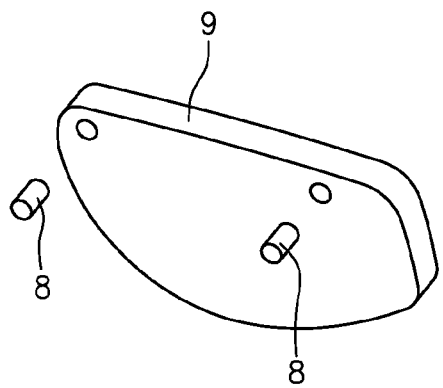
Figure 35C:
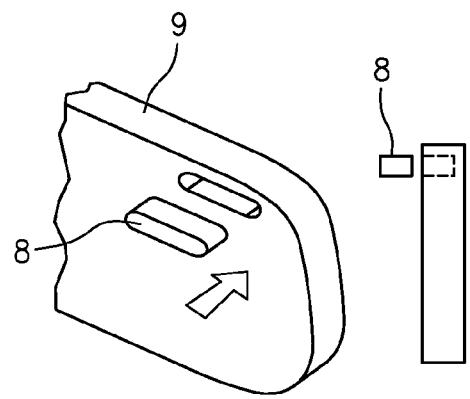

FIGS. 35A-35C illustrate embodiments in which a pocket or pockets are formed at least partially through the thickness of a lens. That is, the pocket in the lens may be formed through the thickness of the lens (a "through hole") or the pocket may end within the thickness of the lens (a "blind hole"). Suitably sized and shaped magnets or magnetic material may be placed within such pockets and secured by any known method.

While various embodiments have been chosen to illustrate the invention, it will be understood by those skilled in the art that various changes and modifications can be made therein without departing from the scope of the invention as defined in the appended claims.

What is claimed is:

1. A lens apparatus for removably mounting a primary lens to an eyeglass frame comprising a lens and at least one lens magnetic member, the lens comprising:
   a lens front surface having a front circumferential edge;
   a lens rear surface having a rear circumferential edge spaced a distance from said front circumferential edge;
   a lens thickness spaced between the front lens surface and the rear lens surface;

a lens circumferential edge surface spaced between the front circumferential edge and the rear circumferential edge; and a lens cavity extending from the circumferential edge surface and at least partially through the lens thickness, the cavity having a proximal cavity portion proximal to the circumferential edge having a first cavity dimension, wherein the proximal cavity portion interrupts the lens circumferential edge surface for a portion of the circumference; and the lens cavity having a distal cavity portion distal from the circumferential edge and having a second cavity dimension;

wherein the at least one lens magnetic member comprises:
a magnetic member front surface;
a magnetic member rear surface;
a magnetic member edge surface; wherein
the lens magnetic member having first portion with a first magnetic member dimension sized to closely fit within the first cavity portion and a second lens magnetic member portion sized to closely fit within the second cavity portion.

2. The lens apparatus according to claim 1 wherein a portion of at least one of the lens magnetic member front surface, rear surface, and edge surface is substantially flush with at least one of the lens front surface, the lens rear surface, and the lens edge surface.

3. The lens apparatus according to claim 1 wherein a portion of at least one of the lens magnetic member front surface, rear surface, and edge surface is not substantially flush with at least one of the lens front surface, the lens rear surface, and the lens edge surface.

4. The lens apparatus according to claim 1 wherein the second cavity dimension is greater than the first cavity dimension.

5. The lens apparatus according to claim 1 wherein the cavity is generally trapezoidal in shape.

6. The lens apparatus according to claim 1 wherein the cavity is generally L-shaped in cross-section.

7. The lens apparatus according to claim 1 wherein at least one of the lens magnet edge, front, and rear surfaces includes a groove formed at least partially on a surface.

8. The lens apparatus according to claim 1 wherein the lens cavity further comprises one or more secondary cavities extending from the distal portion of the lens cavity generally in a direction away from the proximal portion.

9. An eyeglass assembly comprising a primary eyeglass frame adapted for removable mounting of a primary lens thereto, the assembly further comprising:

at least one primary lens having a front surface, a rear surface, a circumferential edge thickness, a lens circumferential edge surface, and a lens cavity extending from the circumferential edge surface and at least partially through the lens thickness, the lens cavity having a proximal cavity portion proximal to the circumferential edge having a first cavity dimension, wherein the proximal cavity portion interrupts the lens circumferential edge surface for a portion of the circumference, the lens cavity having a distal cavity portion distal to the circumferential edge having a second cavity dimension;

at least one lens magnetic member configured to closely engage within the lens cavity, having a first portion with a first dimension sized to closely fit within the proximal cavity portion and a second portion with a second dimension sized to closely fit within the distal cavity portion;

a primary eyeglass frame comprising at least one partial lens rim portion, the at least one partial lens rim portion comprising:
a front frame portion having a front surface;
a rear frame portion separated a distance from and opposing the front frame surface;
a connecting frame portion connecting the front frame portion and the rear frame portion, the connecting portion comprising;
a mounting surface; and
at least one frame cavity extending through the connecting frame portion, the at least one frame cavity having,
a first frame cavity portion proximal to the mounting surface having a first frame cavity dimension, and
a second frame cavity portion distal from the mounting surface having a second frame cavity dimension larger than the first frame cavity dimension; and
at least one frame magnetic member configured to closely engage within the at least one frame cavity such that at least a portion of a frame magnetic member edge surface is substantially flush with the mounting surface.

10. A lens apparatus for removably mounting a primary lens to an eyeglass frame comprising a lens and at least one lens magnetic member, the lens comprising:
a lens front surface having a front circumferential edge;
a lens rear surface having a rear circumferential edge spaced a distance from said front circumferential edge;
a lens thickness spaced between the front lens surface and the rear lens surface;
a lens circumferential edge surface spaced between the front circumferential edge and the rear circumferential edge; and
a lens recess extending from the front, rear or both lens surfaces partially through the lens thickness and from the circumferential edge surface,
the lens recess having a first recess portion proximal to either of the front or rear surface or both lens surfaces having a first dimension, wherein the first recess portion interrupts either of the front or rear surface or both lens surfaces for a portion of a width of the lens surface; and
the lens recess having a second recess portion proximal to the circumferential edge having a second recess dimension, wherein the second recess portion interrupts the lens circumferential edge surface for a portion of the circumference;
the at least one lens magnetic member also comprising a mechanical fastener;
the mechanical fastener having
a first fastening edge sized to fit securely within the edge of the first recess portion and
a second fastening edge sized to fit securely within the edge of the second recess portion,
the mechanical fastener being formed to fit within the lens recess portions such that the outer surfaces of the lens magnetic member are substantially flush with either of the front or rear lens surface or both lens surfaces and with the lens circumferential edge surface.

* * * * *